United States Patent
Ross, Jr. et al.

(10) Patent No.: US 6,348,627 B1
(45) Date of Patent: *Feb. 19, 2002

(54) ARYL AND HETEROARYLCYCLOPROPYL OXIME ETHERS AND THEIR USE AS FUNGICIDES

(75) Inventors: Ronald Ross, Jr., Jamison; Duyan Vuong Nguyen, Philadelphia; Edward Michael Szapacs, Center Valley; Frisby Davis Smith, North Wales; Steven Howard Shaber, Horsham, all of PA (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/572,487

(22) Filed: May 15, 2000

Related U.S. Application Data

(63) Continuation-in-part of application No. 09/238,196, filed on Jan. 27, 1999, now Pat. No. 6,063,956.

(51) Int. Cl.⁷ .................... C07C 233/05; A01N 37/18

(52) U.S. Cl. .................... 564/165; 514/503; 514/531; 514/618; 514/619; 558/256; 560/35; 562/440

(58) Field of Search .................. 514/531, 503, 514/618, 619; 558/256; 560/35; 562/440; 564/165

(56) References Cited

U.S. PATENT DOCUMENTS

| | | | |
|---|---|---|---|
| 5,194,662 A | 3/1993 | Brand et al. | 560/35 |
| 5,292,759 A | 3/1994 | Brand et al. | 514/339 |
| 6,063,956 A | * 5/2000 | Ross et al. | 560/35 |

FOREIGN PATENT DOCUMENTS

WO    WO 98/47886    10/1998

* cited by examiner

Primary Examiner—Shailendra Kumar
(74) Attorney, Agent, or Firm—Thomas D. Rogerson

(57) ABSTRACT

Compounds with fungicidal and insecticidal properties having formula

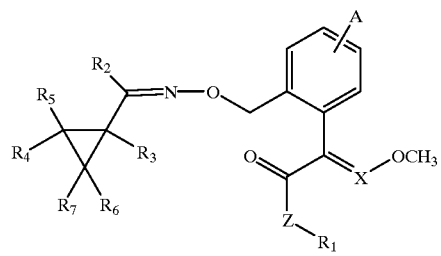

wherein X is N or CH; Z is O, S or $NR_8$; A is hydrogen, halo, cyano, $(C_1-C_{12})$alkyl, or $(C_1-C_{12})$alkoxy; $R_1$ and $R_8$ are independently hydrogen or $(C_1-C_4)$alkyl; $R_2$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, aryl, aralkyl, heterocyclic, heterocyclic $(C_1-C_4)$alkyl or $C(R_{10})$=N—$OR_9$; $R_3$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, aryl, aralkyl, aryl$(C_3-C_7)$cycloalkyl, heterocyclic or heterocyclic$(C_1-C_4)$alkyl; $R_4$ and $R_5$ are independently hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, halo, cyano, $(C_1-C_4)$alkoxycarbonyl, aryl, aralkyl, aryl$(C_3-C_7)$cycloalkyl, heterocyclic or heterocyclic$(C_1-C_4)$alkyl; $R_6$ is hydrogen, $(C_1-C_{12})$alkyl, halo$(C_1-C_{12})$alkyl, $(C_3-C_7)$cycloalkyl, halo $(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, halo, cyano, $(C_1-C_4)$alkoxycarbonyl, aryl, aralkyl, aryl $(C_3-C_7)$cycloalkyl, heterocyclic or heterocyclic $(C_1-C_4)$alkyl; $R_7$ is aryl, aralkyl, heterocyclic or heterocyclic$(C_1-C_4)$alkyl; $R_9$ is hydrogen, $(C_1-C_{12})$alkyl, halo$(C_1-C_{12})$alkyl, $(C_2-C_8)$alkenyl, halo$(C_2-C_8)$alkenyl, $(C_2-C_8)$alkynyl, halo$(C_2-C_8)$alkynyl, $(C_1-C_4)$alkylcarbonyl, $(C_1-C_4)$alkoxycarbonyl, aryl, or aralkyl; and $R_{10}$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, aryl, aralkyl, heterocyclic, or heterocyclic$(C_1-C_4)$alkyl.

12 Claims, No Drawings

ARYL AND HETEROARYLCYCLOPROPYL OXIME ETHERS AND THEIR USE AS FUNGICIDES

This application is a CIP of 09/238,196, filed Jan. 27, 1999, now U.S. Pat. No. 6,063,956.

The present invention relates to certain aryl cyclopropyl oxime ether compounds, compositions containing these compounds, and methods for controlling fungi by the use of a fungitoxic amount of these compounds.

Compounds having certain oxime ether structures are disclosed in U.S. Pat. Nos. 5,194,662 and 5,292,759. We have discovered a group of cyclopropyl oxime ethers which possess a substituted aryl and heterocyclic moieties which possess broad spectrum fungicidal properties.

The cyclopropyloxime ethers of the present invention have the Formula (I)

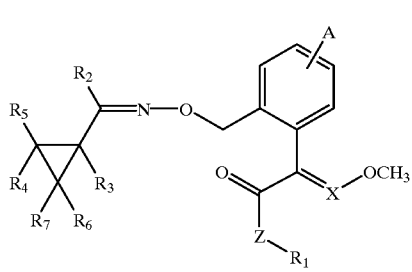

wherein X is N or CH; Z is O, S, or $NR_8$;

A is hydrogen, halo, cyano, $(C_1-C_{12})$alkyl, or $(C_1-C_{12})$alkoxy;

$R_1$ and $R_8$ are independently hydrogen or $(C_1-C_4)$alkyl;

$R_2$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, or cyano;

$R_3$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, or halo$(C_2-C_8)$alkynyl;

$R_4$ and $R_5$ are independently hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, halo, cyano, or $(C_1-C_4)$alkoxycarbonyl; and wherein A) $R_7$ is aryl, arylalkyl, heterocyclic or heterocyclic $(C_1-C_4)$alkyl wherein the aryl or heterocyclic ring is substituted with from 2 to 5 substituents and wherein the positions on the aryl or heterocyclic ring adjacent to the bond to the cyclopropyl ring are both substituted and $R_6$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, or halo$(C_2-C_8)$alkynyl; or B) $R_7$ is aryl, arylalkyl, heterocyclic or heterocyclic $(C_1-C_4)$alkyl wherein the aryl or heterocyclic ring is unsubstituted or substituted from 1 to 4 substituents wherein at least one of the positions on the aryl or heterocyclic ring adjacent to the bond to the cyclopropyl ring is a hydrogen and $R_6$ is $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, or halo$(C_2-C_8)$alkynyl; and their salts, complexes, enantiomorphs, and stereoisomers; and mixtures thereof.

The aforementioned $(C_1-C_{12})$alkyl, $(C_2-C_8)$alkenyl, $(C_2-C_8)$alkynyl and $(C_3-C_7)$cycloalkyl groups may be optionally and independently substituted with up to three substituents selected from nitro, halomethyl, $(C_1-C_4)$alkoxycarbonyl, and cyano.

The term alkyl includes both branched and straight chain alkyl groups from 1 to 12 carbon atoms. Typical alkyl groups are methyl, ethyl, n-propyl, iso-propyl, n-butyl, sec-butyl, isobutyl, t-butyl, n-pentyl, isopentyl, n-hexyl, n-heptyl, isooctyl, nonyl, decyl, undecyl, dodecyl and the like. The term haloalkyl refers to an alkyl group substituted with from 1 to 3 halogens.

The term alkenyl refers to an ethylenically unsaturated hydrocarbon group, straight or branched, having a chain length of from 2 to 8 carbon atoms and 1 or 2 ethylenic bonds. The term haloalkenyl refers to an alkenyl group substituted with from 1 to 3 halogen atoms. The term alkynyl refers to an unsaturated hydrocarbon group, straight or branched, having a chain length of from 2 to 8 carbon atoms and 1 or 2 acetylenic bonds.

The term aryl includes phenyl and naphthyl which maybe substituted with up to four substituents independently selected from halogen, cyano, nitro, trihalomethyl, trihalomethoxy, phenyl, phenoxy, $(C_1-C_4)$alkyl, $(C_3-C_7)$cycloalkyl, $(C_2-C_8)$alkenyl, $(C_1-C_4)$alkoxy, $(C_1-C_4)$alkylthio, $(C_1-C_4)$alkylsulfoxide, halo$(C_1-C_4)$alkyl, halo$(C_1-C_4)$alkoxy, halo$(C_3-C_7)$cycloalkyl, halo$(C_2-C_8)$alkenyl, or $(C_1-C_4)$alkoxycarbonyl. Typical phenyl substituents, wherein at least one of the positions on the phenyl ring adjacent to the bond to the cyclopropyl ring is substituted with hydrogen include but are not limited to 2-chloro, 3-chloro, 4-chloro, 2-fluoro, 3-fluoro, 4-fluoro, 2-bromo, 3-bromo, 4-bromo, 2-methyl, 3-methyl, 4-methyl, 2-trifluoromethyl, 3-trifluoromethyl, 4-trifluoromethyl, 2-methoxy, 3-methoxy, 4-methoxy, 2-trifluoromethoxy, 3-trifluoromethoxy, 4-trifluoromethoxy, 2-cyano, 3-cyano, 4-cyano, 2,3-dichloro, 2,3-difluoro, 2,3-dibromo, 2,3-dimethyl, 2,3-dimethoxy, 2,3-bis(trifluoromethyl), 2,3bis-(trifluoromethoxy), 2,4-difluoro, 2,4-dichloro, 2,4-dibromo, 2,4-dimethyl, 2,4-dimethoxy, 2,4-bis(trifluoromethyl), 2,4-bis(trifluoromethoxy), 2,5-difluoro, 2,5-dichloro, 2,5-dibromo, 2,5-dimethyl, 2,5-dimethoxy, 2,5-bis(trifluoromethyl), 2,5-bis-(trifluoromethoxy), 3,4-difluoro, 3,4-dichloro, 3,4-dibromo, 3,4-dimethyl, 3,4-dimethoxy, 3,4-bis(trifluoromethyl), 3,4-bis(trifluoromethoxy), 3,5-difluoro, 3,5-dichloro, 3,5-dibromo, 3,5-dimethyl, 3,5-bis(trifluoromethyl), 3,5-bis(trifluoromethoxy), 2,3,4-trifluoro, 2,3,4-trichloro, 2,3,4-tribromo, 2,3,4-trimethyl, 2,3,4-trimethoxy, 2,3,4-tris(trifluoromethyl), 2,3,4-tris(trifluoromethoxy), 2,3,5-trifluoro, 2,3,5-trichloro, 2,3,5-tribromo, 2,3,5-trimethyl, 2,3,5-tris(trifluoromethyl), 2,3,5-tris(trifluoromethoxy), 2,4,5-trifluoro, 2,4,5-trichloro, 2,4,5-tribromo, 2,4,5-trimethyl, 2,4,5-trimethoxy, 2,4,5-tris(trifluoromethyl), 2,4,5-tris(trifluoromethoxy), 3,4,5-trifluoro, 3,4,5-trichloro, 3,4,5-tribromo, 3,4,5-trimethyl, 3,4,5-trimethoxy, 3,4,5-tris(trifluoromethyl), 3,4,5-tris(trifluoromethoxy), 2,3,4,5-tetrafluoro, 2,3,4,5-tetrachloro, 2,3,4,5-tetrabromo, 2,3,4,5-tetramethyl, 2,3,4,5-tetramethoxy, 2,3,4,5-tetra(trifluoromethyl), and 2,3,4,5-tetra(tetrafluoromethoxy).

Typical phenyl substituents, where both positions on the phenyl ring adjacent to the bond to the cyclopropyl rings are substituted include but are not limited to 2,6-dichloro, 2,3,6-trichloro, 2,4,6-trichloro, 2,6-difluoro, 2,3,6-trifluoro, 2,4,6-trifluoro, 2,6-dibromo, 2,3,6-tribromo, 2,4,6-tribromo 2,3,4,6-tetrachloro, 2,3,5,6-tetrachloro, 2,3,4,5,6-pentachloro, 2,3,4,6-tetrabromo, 2,3,5,6-tetrabromo, 2,3,4,5,6-pentabromo, 2,3,4,6-tetrafluoro, 2,3,5,6-tetrafluoro, 2,3,4,5,6-pentafluoro, 2,6-dimethyl, 2,3,6-trimethyl, 2,4,6-trimethyl, 2,6-dimethoxy, 2,3,6-trimethoxy, 2,4,6-trimethoxy, 2,6-diethoxy, 2,3,6-triethoxy, 2,4,6-triethoxy, 2,3,4,6-tetramethyl, 2,3,5,6-tetramethyl, 2,3,4,5,6-pentamethyl, 2,3,4,6-tetramethoxy, 2,3,5,6-tetramethoxy, 2,3,4,5,6-pentamethoxy, 2,3,4,6-tetraethoxy, 2,3,5,6-tetraethoxy, 2,3,4,5,6-pentaethoxy, 2,6-dicyano, 2,3,6-tricyano, 2,4,6-tricyano, 2,6-dinitro, 2,6-diphenyl, 2,6-diphenoxy, 2,6-dibenzyl, 2,6-bis(trifluoromethyl), 2,3,6-tris(trifluoromethyl), 2,4,6-tris-(trifluoromethyl), 2,3,4,6-tetra(trifluoromethyl), 2,3,5,6-tetra(trifluoromethyl), 2,3,4,5,6-penta(trifluoromethyl), 2,6-bis-(trifluoromethoxy), 2,3,6-tris(trifluoromethoxy), 2,4,6-tris(trifluoromethoxy), 2,3,4,5-tetra(trifluoromethoxy), 2,3,4,6-tetra-(trifluoromethoxy), 2,3,5,6-tetra(trifluoromethoxy), 2,3,4,5,6-penta(trifluoromethoxy), 2-bromo-6-chloro, 2-bromo-6-fluoro, 2-bromo-6-(trifluoromethyl), 2-bromo-6-methyl, 2-bromo-6-methoxy, 2-bromo-6-(trifluoromethoxy), 2-bromo-6-cyano, 2-chloro-6-fluoro, 2-chloro-6-(trifluoromethyl), 2-chloro-6-methyl, 2-chloro-6-methoxy, 2-chloro-6-trifluoromethoxy), 2-chloro-6-cyano, 2-fluoro-6-(trifluoromethyl), 2-fluoro-6-methyl, 2-fluoro-6-methoxy, 2-fluoro-6-(trifluoromethoxy), 6-cyano-2-fluoro, 2-methyl-6-(trifluoromethyl), 6-methoxy-2-methyl, 2-methyl-6-(trifluoromethoxy), 6-cyano-2-methyl, 3,6-dichoro-2-fluoro, 3-chloro-2,6-difluoro, 4-chloro-2,6-difluoro, 2-bromo-3,6-dichoro, 2,3-dibromo-6-chloro, 3-chloro-2,6-dibromo, 2,6-dichloro-3-fluoro, 2,3-dichloro-6-fluoro, 2-chloro-3,6-difluoro, 3-bromo-2,6-dichloro, 3-bromo-2,6-fluoro, 3-bromo-6-chloro-2-fluoro, 2-bromo-5-chloro-6-fluoro, 2,6-dibromo-3-fluoro, 2,5-dibromo-6-fluoro, 2,4-dichloro-6-fluoro, 2,6-chloro-4-fluoro, 2,4,-dichloro-6-bromo, 2,6-dichloro-4-bromo, 2,4-difluoro-6-chloro, 2,4-difluoro-6-bromo, 2,6-difluoro-4-bromo, 2,4-dibromo-6-fluoro, 2,4-dibromo-6-chloro, 2,6-dibromo-4-chloro, 2,6-dibromo-4-fluoro, 2,4-dichloro-6-methyl, 2,6-dichloro-4-methyl, 2-chloro-4,6-dimethyl, 4-chloro-2,6-dimethyl, 2,4-difluoro-6-methyl, 2,6-difluoro-4-methyl, 2-fluoro-4,6-dimethyl, 4-fluoro-2,6-dimethyl, 2,4-dibromo-6-methyl, 2,6-dibromo-4-methyl, 2-bromo-4,6-dimethyl, 4-bromo-2,6-dimethyl, 2,4-dichloro-6-methoxy, 2,6-dichloro-4-methoxy, 2-chloro-4,6-dimethoxy, 4-chloro-2,6-dimethoxy, 2,4-difluoro-6-methoxy, 2,6-difluoro-4-methoxy-, 2-fluoro-4,6-dimethoxy, 4-fluoro-2,6-dimethoxy, 2,4-dibromo-6-methoxy, 2,6-dibromo-4-methoxy, 4-bromo-2,6-dimethoxy, 4-bromo-2,6-dimethoxy, 2,4-dichloro-6-(trifluoromethyl), 2,6-dichloro-4-(trifluoromethyl), 2-chloro-4,6-bis(trifluoromethyl), 4-chloro-2,6-bis(trifluoromethyl), 2,4-difluoro-6-(trifluoromethyl), 2,6-difluoro-4-(trifluoromethyl), 2-fluoro-4,6-bis(trifluoromethyl), 4-fluoro-2,6-bis(trifluoromethyl), 2,4-dibromo-6-(trifluoromethyl), 2,6-dibromo-4-(trifluoromethyl), 2-bromo-4,6-bis(trifluoromethyl), 4-bromo-2,6-bis(trifluoromethyl), 2-chloro-4,6-bis(trifluoromethoxy), 4-chloro-2,6-bis(trifluoromethoxy), 2,4-difluoro-6-(trifluoromethoxy), 2,6-difluoro-4-(trifluoromethoxy), 2-fluoro-4,6-bis(trifluoromethoxy), 4-fluoro-2,6-bis(trifluoromethoxy), 2,4-dibromo-6-(trifluoromethoxy), 2,6-dibromo-4-(trifluoromethoxy), 2-bromo-4,6-bis(trifluoromethoxy), 4-bromo-2,6-bis(trifluoromethoxy), 4,6-dichloro-2-nitro, 4,6-dibromo-2-nitro, 4,6-difluoro-2-nitro, 2,6-dichloro-4-nitro, 2-bromo-3,4,6-trichloro, 6-fluoro-2,4,5-trichloro, 6-chloro-2,4,5-tribromo, 6-fluoro-2,4,5-tribromo, 2-bromo-3,4,6-trifluoro, 2-chloro-3,4,6-trifluoro, 6-methyl-2,4,5-trichloro, 6-methyl-2,4,5-tribromo, 6-methyl-3,4,6-trifluoro, 6-(trifluoromethyl)-2,4,5-trichloro, 6-(trifluoromethyl)-2,4,5-tribromo, 2-(trifluoromethyl)-3,4,6-trifluoro, 6-(trifluoromethoxy)-2,4,5-tribromo, 2-(trifluoromethoxy)-3,4,6-trifluoro, 6-(trifluoromethoxy)-2,4,5-trichloro, 2-bromo-3,5,6-trichloro, 6-fluoro-2,3,5-trichloro, 6-chloro-2,3,5-tribromo, 6-fluoro-2,3,5-tribromo, 2-bromo-3,5,6-trifluoro, 2-chloro-3,5,6-trifluoro, 6-methyl-2,3,5-trichloro, 6-methyl-2,3,5-tribromo, 2-methyl-3,5,6-trifluoro, 6-(trifluoromethyl)-2,3,5-trichloro, 6-(trifluoromethyl)-2,3,5-tribromo, 2-(trifluoromethyl)-3,5,6-trifluoro, 2-(trifluoromethoxy)-3,5,6-trichloro, 6-(trifluoromethoxy)-2,3,5-tribromo, 2-(trifluoromethoxy)-3,5,6-trifluoro, 4-bromo-2,3,5,6-tetrachloro, 4-fluoro-2,3,5,6-tetrachloro,4-chloro-2,3,5,6-tetrabromo-, 4-fluoro-2,3,5,6-tetrabromo, 4-chloro-2,3,5,6-tetrafluoro, 4-bromo-2,3,5,6-tetrafluoro, 2-bromo-3,4,5,6-tetrachloro, 6-fluoro-2,3,4,5-tetrachloro-, 2-chloro-3,4,5,6-tetrafluoro, 2-bromo-3,4,5,6-tetrafluoro, 2-chloro-3,4,5,6-tetrabromo, 2-fluoro-3,4,5,6-tetrabromo, 4-methyl-2,3,5,6-tetrachloro, 4-methyl-2,3,5,6-tetrabromo, 4-methyl-2,3,5,6-tetrafluoro, 2,3,5,6-tetrachloro-4-(trifluoromethyl), 2,3,5,6-tetrabromo-4-(trifluoromethyl), 2,3,5,6-tetrafluoro-4-(trifluoromethyl), 2,3,5,6-tetrachloro-4-(trifluoromethoxy), 2,3,5,6-tetrabromo-4-(trifluoromethoxy, 2,3,5,6-tetrafluoro-4-(trifluoromethoxy), 6-methyl-2,3,4,5-tetrachloro, 6-methyl-2,3,4,5-tetrabromo, 2-methyl-3,4,5,6-tetrafluoro, 2,3,4,5-tetrachloro-6-(trifluoromethyl), 2,3,4,5-tetrabromo-6-(trifluoromethyl), 3,4,5,6-tetrafluoro-2-(trifluoromethyl), 2,3,4,5-tetrachloro-6-(trifluoromethoxy), 2,3,4,5-tetrabromo-6-(trifluoromethoxy), and 3,4,5,6-tetrafluoro2-(trifluoromethoxy).

The term heterocyclic refers to a substituted 6 membered unsaturated ring selected from 3- or 4-pyridinyl, 5-pyrimidinyl, 3-pyridazinyl or a 5 membered unsaturated ring selected from 3-thienyl, 3-furyl, 3-pyrrolyl, 4-isoxazolyl, 4-isothiazolyl or 4-pyrazolyl wherein both the positions on the heterocyclic ring adjacent to the bond to the cyclopropyl ring are substituted and the ring is substituted with from 2 to 4 substituents independently selected from $(C_1-C_4)$ alkyl, $(C_3-C_7)$cycloalkyl, trihalomethyl, trihalomethoxy, halogen, cyano, $(C_1-C_4)$alkoxycarbonyl, nitro, phenyl, and phenoxy. The term heterocyclic also refers to a substituted or unsubstituted 6 membered unsaturated ring containing one, two or three heteroatoms, preferably one, two or three heteroatoms independently selected from oxygen, nitrogen, and sulfur or a 5 membered unsaturated ring containing one, two or three heteroatoms, preferably one or two heteroatoms independently selected from oxygen, nitrogen, and sulfur wherein the heterocyclic ring is unsubstituted or is substituted with from 1 to 3 substituents wherein at least one of the positions of the heterocyclic ring adjacent to the bond to the cyclopropyl ring is a hydrogen substituent. Examples of heterocycles include but are not limited to 2-, 3- or 4-pyridinyl, pyrazinyl, 4-, or 5-pyrimidinyl, pyridazinyl, pyrazole, imidazolyl, 2 or 3-thienyl, 2 or 3-furyl, 3-pyrrolyl, oxazolyl, isoxazolyl, thiazolyl, isothiazolyl, oxadiazolyl, and thiadiazolyl. These rings may be optionally substituted with up from 1 to 3 substituents independently selected from $(C_1-C_4)$ alkyl, $(C_3-C_7)$cycloalkyl, trihalomethyl, halogen, cyano, $(C_1-C_4)$ alkoxycarbonyl, nitro, phenyl, and phenoxy.

The term arylalkyl is used to describe a group wherein the alkyl chain is from 1 to 10 carbon atoms and can be branched or straight chain, preferably a straight chain, with the aryl portion, as defined above, forming a terminal portion of the arylalkyl moiety. Typical arylalkyl moieties are optionally substituted benzyl, phenethyl, phenpropyl, and phenbutyl moieties.

Typical benzyl moieties wherein at least one of the positions on the phenyl ring, adjacent to the methylene which is bonded to the cyclopropyl ring, is substituted with hydrogen include but are not limited to 2-chlorobenzyl, 3-chlorobenzyl, 4-chlorobenzyl, 2-fluorobenzyl, 3-fluorobenzyl, 4-fluorobenzyl, 2-bromobenzyl, 3-bromobenzyl, 4-bromobenzyl, 2-trifluoromethylbenzyl, 3-trifluoromethylbenzyl, 4-trifluoromethylbenzyl, 2-methylbenzyl, 3-methylbenzyl, 4-methylbenzyl 2,3-difluorobenzyl, 2,3-dichlorobenzyl, 2,3-dibromobenzyl, 2,3-dimethylbenzyl, 2,4-difluorobenzyl, 2,4-dichlorobenzyl, 2,4-dibromobenzyl, 2,4-dimethylbenzyl, 2,5-difluorobenzyl, 2,5-dichlorobenzyl, 2,5-dibromobenzyl, 2,5-dimethylbenzyl, 3,4-difluorobenzyl, 3,4-dichlorobenzyl, 3,4-dibromobenzyl, 3,4-dimethylbenzyl, 3,5-difluorobenzyl, 3,5-dichlorobenzyl, 3,5-dibromobenzyl, 3,5-dimethylbenzyl, 2,3,4-triifluorobenzyl, 2,3,4-trichlorobenzyl, 2,3,4-tribromobenzyl, and 3,4,5-trichlorobenzyl.

Typical benzyl moieties wherein both positions on the phenyl ring, adjacent to the methylene which is bonded to the cyclopropyl ring, are substituted include but are not limited to 2,6-dichlorobenzyl, 2,3,6-trichlorobenzyl, ]2,4,6-trichlorobenzyl, 2,6-difluorobenzyl, 2,3,6-fluorobenzyl, 2,4,6-trifluorobenzyl, 2,6-bis(trifluoromethyl)benzyl, 2,3,6-tris(trifluoromethyl)benzyl, 2,4,6-tris(trifluoromethyl)benzyl, 2,3,4,6-tetrachlorobenzyl, 2,3,5,6-tetrachlorobenzyl, 2,3,4,5,6-pentachlorobenzyl, 2,3,4,6-tetrabromobenzyl, 2,3,5,6-tetrabromobenzyl, 2,3,4,5,6-pentabromobenzyl, 2,3,4,6-tetrafluorobenzyl, 2,3,5,6-tetrafluorobenzyl, and 2,3,4,5,6-pentafluorobenzyl. Typical phenethyl moieties wherein at least one of the positions on the phenyl ring, adjacent to the ethyl moiety which is bonded to the cyclopropyl ring, is substituted with hydrogen include but are not limited to 2-(2-chlorophenyl)ethyl, 2-(3-chlorophenyl)ethyl, 2-(4-chlorophenyl)ethyl, 2-(2-fluorophenyl)ethyl, 2-(3-fluorophenyl)ethyl, 2-(4-fluorophenyl)ethyl, 2-(2-methylphenyl)ethyl, 2-(3-methylphenyl)ethyl, 2-(4-methylphenyl)ethyl, 2-(4-trifluoromethylphenyl)ethyl, 2-(2,4-dichlorophenyl)ethyl, and 2-(3,5-dimethoxyphenyl)ethyl. Typical phenethyl moieties wherein both positions on the phenyl ring, adjacent to the ethyl moiety which is bonded to the cyclopropyl ring, are substituted include but are not limited to 2-(2,6-dichlorophenyl)ethyl, 2-(2,3,6-trichlorophenyl)ethyl, 2-(2,4,6-trichlorophenyl)ethyl, 2-(2,6-difluorophenyl)ethyl, 2-(2,3,6-trifluorophenyl)ethyl, 2-(2,4,6-trifluorophenyl)ethyl, 2-(2,6-dimethylphenyl)ethyl, 2-(2,3,6-trimethylphenyl)ethyl, 2-(2,4,6-trimethylphenyl)ethyl, 2-(2,6-bis(trifluoromethyl)phenyl)ethyl, 2-(2,3,6-tris(trifluoromethyl)phenyl)ethyl, 2-(2,4,6-tris(trifluoromethyl)phenyl)ethyl, 2-(2,6-dimethoxyphenyl)ethyl, 2-(2,3,6-trimethoxyphenyl)ethyl, and 2-(2,4,6-trimethoxyphenyl)ethyl. Typical phenpropyl moieties wherein at least one of the positions on the phenyl ring, adjacent to the propyl moiety which is bonded to the cyclopropyl ring, is substituted with hydrogen include but are not limited to 3-phenylpropyl, 3-(2-chlorophenyl)propyl, 3-(3-chlorophenyl)propyl, 3-(4-chlorophenyl)propyl, 3-(2,4-dichlorophenyl)propyl, 3-(2-fluorophenyl)propyl, 3-(3-fluorophenyl)propyl, 3-(4-fluorophenyl)propyl, 3-(2-methylphenyl)propyl, 3-(3-methylphenyl)propyl, 3-(4-methylphenyl)propyl, 3-(4-trifluoromethylphenyl)propyl, 3-(2,4-dichlorophenyl)propyl, and 3-(3,5-dimethylphenyl)propyl. Typical phenpropyl moieties wherein both positions on the phenyl ring, adjacent to the propyl moiety which is bonded to the cyclopropyl ring, are substituted include but are not limited to 3-(2,6-dichlorophenyl)propyl, 3-(2,3,6-trichlorophenyl)propyl, 3-(2,4,6-trichlorophenyl)propyl, 3-(2,6-difluorophenyl)propyl, 3-(2,3,6-trifluorophenyl)propyl, 3-(2,4,6-trifluorophenyl)propyl, 3-(2,6-dimethylphenyl)propyl, 3-(2,3,6-trimethyl-phenyl)propyl, 3-(2,4,6-trimethylphenyl)propyl and 3-(2,6-bis(trifluoromethyl)phenyl)propyl. Typical phenbutyl moieties wherein at least one of the positions on the phenyl ring, adjacent to the butyl moiety which is bonded to the cyclopropyl ring, is substituted with hydrogen include but are not limited to 4-phenylbutyl, 4-(2-chlorophenyl)butyl, 4-(3-chlorophenyl)butyl, 4-(4-chlorophenyl)butyl, 4-(2-fluorophenyl)butyl, 4-(3-fluorophenyl)butyl, 4-(4-fluorophenyl)butyl, 4-(2-methylphenyl)butyl, 4-(3-methylphenyl)butyl, 4-(4-methylphenyl)butyl and 4-(2,4-dichlorophenyl)butyl. Typical phenbutyl moieties wherein both positions on the phenyl ring, adjacent to the butyl moiety which is bonded to the cyclopropyl ring, are substituted include but are not limited to 4-(2,6-di-chlorophenyl)butyl, 4-(2,3,6-trichlorophenyl)butyl, 4-(2,4,6-trichlorophenyl)butyl, 4-(2,6-difluorophenyl)butyl, 4-(2,3,6-trifluorophenyl)butyl, 4-(2,4,6-trifluorophenyl)butyl, 4-(2,6-dimethylphenyl)butyl, 4-(2,3,6-trimethylphenyl)butyl, 4-(2,4,6-trimethylphenyl)butyl and 4-(2,6-bis(trifluoromethyl)phenyl)butyl.

Halogen or halo includes iodo, fluoro, bromo and chloro moieties.

The compounds of the general Formula I may be obtained in preparation as E/Z isomeric mixtures. These isomers can be separated into individual components by conventional means. The substituted cyclopropanes of Formula I may be obtained in preparation as cis and trans isomeric mixtures which can be separated into individual components by conventional means. Both the individual isomeric compounds and mixtures thereof form subjects of the invention and can be used as fungicides and insecticides.

One preferred embodiment of this invention is the compounds, enantiomorphs, salts and complexes of Formula I wherein X is CH or N; Z is O or NH; A=$R_3$=$R_4$=$R_5$=hydrogen; $R_1$ and $R_2$ are $CH_3$; $R_7$ is 2,6-dichlorophenyl or 2,6-difluorophenyl; and $R_6$ is hydrogen.

Another preferred embodiment of this invention is the compounds, enantiomorphs, salts and complexes of Formula I wherein X is CH or N; Z is O or NH; A=$R_3$=$R_4$=$R_5$=hydrogen; $R_1$ and $R_2$ are $CH_3$; $R_7$ is 2,6-dichlorophenyl or 2,6-difluorophenyl; and $R_6$ is ($C_1$–$C_{12}$)alkyl, halo($C_1$–$C_{12}$)alkyl, ($C_3$–$C_7$)cycloalkyl, halo($C_3$–$C_7$)cycloalkyl, ($C_2$–$C_8$)alkenyl, halo($C_2$–$C_8$)alkenyl, ($C_2$–$C_8$)alkynyl, or halo($C_2$–$C_8$)alkynyl.

A more preferred embodiment of this invention is the compounds, enantiomorphs, salts and complexes of Formula I wherein X is CH or N; Z is O or NH; A is hydrogen; $R_1$ and $R_2$ are independently ($C_1$–$C_4$)alkyl; $R_3$, $R_4$, and $R_5$ are hydrogen; $R_7$ is phenyl other than 2,6-dichlorophenyl or 2,6-difluorophenyl such that the positions on the phenyl ring adjacent to the bond to the cyclopropyl rings are substituted, and $R_6$ is selected from hydrogen, ($C_1$–$C_{12}$)alkyl, halo($C_1$–$C_{12}$)alkyl, ($C_3$–$C_7$)cycloalkyl, halo($C_3$–$C_7$)cycloalkyl, ($C_2$–$C_8$)alkenyl, halo($C_2$–$C_8$)alkenyl, ($C_2$–$C_8$)alkynyl, and halo($C_2$–$C_8$)alkynyl.

Another more preferred embodiment of this invention is the compounds, enantiomorphs, salts and complexes of Formula I wherein X is CH or N; Z is O or NH; A is hydrogen; $R_1$ and $R_2$ are independently ($C_1$–$C_4$)alkyl; $R_3$, $R_4$ and $R_5$ are hydrogen; $R_6$ is hydrogen or ($C_1$–$C_{12}$)alkyl; and $R_7$ is 2,3,6-trisubstitutedphenyl, 2,4,6-trisubstitutedphenyl, 2,3,4,6-tetrasubstitutedphenyl, 2,3,5,6-tetrasubstituted, or 2,3,4,5,6-pentasubstitutedphenyl.

An even more preferred embodiment of this invention are the compounds, enantiomorphs, salts and complexes of Formula I wherein X is N; Z is NH; A is hydrogen; $R_1$ and $R_2$ is $CH_3$; $R_3$, $R_4$ and $R_5$ are hydrogen; $R_6$ is hydrogen or $(C_1–C_4)$alkyl; and $R_7$ is 2,3,6-trihalophenyl, 2,4,6-trihalophenyl, 2,3,4,6-tetrahalophenyl, 2,3,5,6-tetrahalophenyl, or 2,3,4,5,6-pentahalophenyl.

Still another preferred embodiment of this invention is the compounds, enantiomorphs, salts and complexes of in Formula I X is CH or N; Z is O or NH; A is hydrogen; $R_1$ and $R_2$ are independently $(C_1–C_4)$alkyl; $R_3$, $R_4$ and $R_5$ are hydrogen; $R_7$ is phenyl, phenylalkyl, or heterocyclic wherein at least one of the positions on the phenyl or heterocyclic ring adjacent to the bond to the cyclopropyl ring is a hydrogen substituent; and $R_6$ is $(C_1–C_{12})$alkyl, halo$(C_1–C_{12})$alkyl, $(C_3–C_7)$cycloalkyl, halo$(C_3–C_7)$cycloalkyl, $(C_2–C_8)$alkenyl, halo$(C_2–C_8)$alkenyl, $(C_2–C_8)$alkynyl, or halo$(C_2–C_8)$alkynyl.

Another more preferred embodiment of this invention is the compounds, enantiomorphs, salts and complexes of Formula I wherein X is N; Z is NH; A is hydrogen; $R_1$ and $R_2$ is $(CH_3)$; $R_3$, $R_4$ and $R_5$ are hydrogen; $R_7$ is phenyl, 2-substitutedphenyl, 3-substitutedphenyl, 4-substitutedphenyl, 2,3-disubstitutedphenyl 2,4-disubstitutedphenyl, 2,5-disubstitutedphenyl, 3,4-disubstitutedphenyl, 3,5-disubstituted, 2,3,4-trisubstitutedphenyl, 2,3,5-trisubstitutedphenyl, 2,4,5-trisubstitutedphenyl, 3,4,5-trisubstitutedphenyl, or 2,3,4,5-tetrasubstitutedphenyl; and $R_6$ is $(C_1–C_4)$alkyl or halo $(C_1–C_4)$alkyl.

A second even more preferred embodiment of this invention is the compounds, enantiomorphs, salts and complexes of Formula II wherein $R_7$ is phenyl, 2-halophenyl, 3-halophenyl, 4-halophenyl, 2,3-dihalophenyl 2,4-dihalophenyl, 2,5-dihalophenyl, 3,4-dihalophenyl, 3,5-dihalophenyl, 2,3,4-trihalophenyl, 2,3,5-trihalophenyl, 2,4,5-trihalophenyl, 3,4,5-trihalophenyl, or 2,3,4,5-tetrahalophenyl, and $R_6$ is $(C_1–C_4)$alkyl.

II

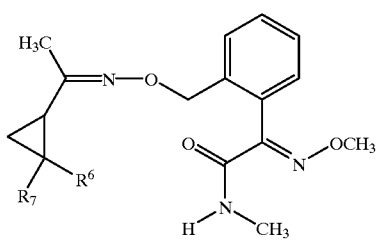

A most preferred embodiment of this invention is the compounds, enantiomorphs, salts and complexes of Formula II wherein $R_7$ is phenyl, 2-chlorophenyl, 3-chlorophenyl, or 4-chlorophenyl, and $R_6$ is $CH_3$.

Typical compounds of Formula I encompassed by the present invention wherein A, $R_3$, $R_4$, and $R_5$ are hydrogen; X is CH and Z is O; and $R_1$ is methyl include those compounds presented in Table 1 of Formula III where $R_2$, $R_6$, and $R_7$ are defined in Table 1.

Formula III

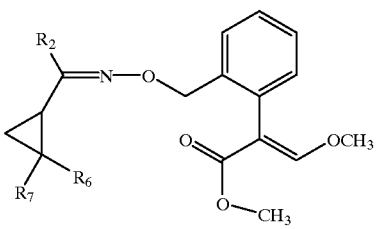

TABLE 1

| Compd # | $R_2$ | $R_6$ | $R_7$ |
|---|---|---|---|
| 1.1 | H | $CH_3$ | Ph |
| 1.2 | H | $CH_3$ | 4-Cl(Ph) |
| 1.3 | H | $CH_3$ | 4-Br(Ph) |
| 1.4 | H | $CH_3$ | 4-F(Ph) |
| 1.5 | H | $CH_3$ | 4-OCH$_3$(Pb) |
| 1.6 | H | $CH_3$ | 4-CF$_3$(Ph) |
| 1.7 | H | $CH_3$ | 4-NO$_2$(Ph) |
| 1.8 | H | $CH_3$ | 2,4-Cl(Ph) |
| 1.9 | H | $CH_3$ | 2,4-F(Ph) |
| 1.10 | H | $CH_3$ | 3,4-F(Ph) |
| 1.11 | $CH_3$ | $CH_3$ | Ph |
| 1.12 | $CH_3$ | $CH_3$ | 2-Cl(Ph) |
| 1.13 | $CH_3$ | $CH_3$ | 3-Cl(Ph) |
| 1.14 | $CH_3$ | $CH_3$ | 4-Cl(Pb) |
| 1.15 | $CH_3$ | $CH_3$ | 2-Br(Ph) |
| 1.16 | $CH_3$ | $CH_3$ | 3-Br(Ph) |
| 1.17 | $CH_3$ | $CH_3$ | 4-Br(Ph) |
| 1.18 | $CH_3$ | $CH_3$ | 2-F(Ph) |
| 1.19 | $CH_3$ | $CH_3$ | 3-F(Ph) |
| 1.20 | $CH_3$ | $CH_3$ | 4-F(Ph) |
| 1.21 | $CH_3$ | $CH_3$ | 2-OCH$_3$(Ph) |
| 1.22 | $CH_3$ | $CH_3$ | 3-OCH$_3$(Ph) |
| 1.23 | $CH_3$ | $CH_3$ | 4-OCH$_3$(Ph) |
| 1.24 | $CH_3$ | $CH_3$ | 2-CH$_3$(Ph) |
| 1.25 | $CH_3$ | $CH_3$ | 3-CH$_3$(Ph) |
| 1.26 | $CH_3$ | $CH_3$ | 4-CH$_3$(Ph) |
| 1.27 | $CH_3$ | $CH_3$ | 2-CF$_3$(Ph) |
| 1.28 | $CH_3$ | $CH_3$ | 3-CF$_3$(Ph) |
| 1.29 | $CH_3$ | $CH_3$ | 4-CF$_3$(Ph) |
| 1.30 | $CH_3$ | $CH_3$ | 2-NO$_2$(Ph) |
| 1.31 | $CH_3$ | $CH_3$ | 3-NO$_2$(Ph) |
| 1.32 | $CH_3$ | $CH_3$ | 4-NO$_2$(Ph) |
| 1.33 | $CH_3$ | $CH_3$ | 2,3-Cl(Ph) |
| 1.34 | $CH_3$ | $CH_3$ | 2,4-Cl(Ph) |
| 1.35 | $CH_3$ | $CH_3$ | 2,5-Cl(Ph) |
| 1.36 | $CH_3$ | $CH_3$ | 3,4-Cl(Ph) |
| 1.37 | $CH_3$ | $CH_3$ | 3,5-Cl(Ph) |
| 1.38 | $CH_3$ | $CH_3$ | 2,3,5-Cl(Ph) |
| 1.39 | $CH_3$ | $CH_3$ | 2,3-F(Ph) |
| 1.40 | $CH_3$ | $CH_3$ | 2,4-F(Ph) |
| 1.41 | $CH_3$ | $CH_3$ | 2,5-F(Ph) |
| 1.42 | $CH_3$ | $CH_3$ | 3,4-F(Ph) |
| 1.43 | $CH_3$ | $CH_3$ | 3,5-F(Ph) |
| 1.44 | $CH_3$ | $CH_3$ | 2,4,5-F(Ph) |
| 1.45 | $CH_3$ | $CH_3$ | 2,4,5-Cl(Ph) |
| 1.46 | $CH_3$ | $CH_3$ | 3,4,5-Cl(Ph) |
| 1.47 | $CH_3$ | $CH_3$ | 2,3,4,5-Cl(Ph) |
| 1.48 | $CH_3$ | $CH_3$ | 2,3,5-F(Ph) |
| 1.49 | $CH_3$ | $CH_3$ | 3,4,5-F(Ph) |
| 1.50 | $CH_3$ | $CH_3$ | 2,3,4,5-F(Ph) |
| 1.51 | $C_2H_5$ | $CH_3$ | Ph |
| 1.52 | $C_2H_5$ | $CH_3$ | 2-Cl(Ph) |
| 1.53 | $C_2H_5$ | $CH_3$ | 3-Cl(Ph) |
| 1.54 | $C_2H_5$ | $CH_3$ | 4-Cl(Ph) |
| 1.55 | $C_2H_5$ | $CH_3$ | 4-Br(Ph) |
| 1.56 | $C_2H_5$ | $CH_3$ | 4-F(Ph) |
| 1.57 | $C_2H_5$ | $CH_3$ | 4-OCH$_3$(Ph) |
| 1.58 | $C_2H_5$ | $CH_3$ | 4-CH$_3$(Ph) |
| 1.59 | $C_2H_5$ | $CH_3$ | 4-NO$_2$(Ph) |
| 1.60 | $C_2H_5$ | $CH_3$ | 2,4-Cl(Ph) |
| 1.61 | $C_2H_5$ | $CH_3$ | 2,4-F(Ph) |

TABLE 1-continued

| Compd # | R₂ | R₆ | R₇ |
|---|---|---|---|
| 1.62 | n-C₃H₇ | CH₃ | Ph |
| 1.63 | n-C₃H₇ | CH₃ | 2-Cl(Ph) |
| 1.64 | n-C₃H₇ | CH₃ | 3-Cl(Ph) |
| 1.65 | n-C₃H₇ | CH₃ | 4-Cl(Ph) |
| 1.66 | n-C₃H₇ | CH₃ | 4-F(Ph) |
| 1.67 | n-C₃H₇ | CH₃ | 3-OCH₃(Ph) |
| 1.68 | n-C₃H₇ | CH₃ | 4-OCH₃(Ph) |
| 1.69 | n-C₃H₇ | CH₃ | 4-CH₃(Ph) |
| 1.70 | n-C₃H₇ | CH₃ | 4-NO₂(Ph) |
| 1.71 | n-C₃H₇ | CH₃ | 2,4-Cl(Ph) |
| 1.72 | n-C₃H₇ | CH₃ | 2,4-F(Ph) |
| 1.73 | iso-C₃H₇ | CH₃ | Ph |
| 1.74 | iso-C₃H₇ | CH₃ | 2-Cl(Ph) |
| 1.75 | iso-C₃H₇ | CH₃ | 3-Cl(Ph) |
| 1.76 | iso-C₃H₇ | CH₃ | 4-Cl(Ph) |
| 1.77 | iso-C₃H₇ | CH₃ | 4-Br(Ph) |
| 1.78 | iso-C₃H₇ | CH₃ | 4-F(Ph) |
| 1.79 | iso-C₃H₇ | CH₃ | 4-OCH₃(Ph) |
| 1.80 | iso-C₃H₇ | CH₃ | 4-CH₃(Ph) |
| 1.81 | iso-C₃H₇ | CH₃ | 4-NO₂(Ph) |
| 1.82 | iso-C₃H₇ | CH₃ | 2,4-Cl(Ph) |
| 1.83 | iso-C₃H₇ | CH₃ | 2,4-F(Ph) |
| 1.84 | n-C₄H₉ | CH₃ | Ph |
| 1.85 | n-C₄H₉ | CH₃ | 2-Cl(Ph) |
| 1.86 | n-C₄H₉ | CH₃ | 3-Cl(Ph) |
| 1.87 | n-C₄H₉ | CH₃ | 4-Cl(Ph) |
| 1.88 | n-C₄H₉ | CH₃ | 4-Br(Ph) |
| 1.89 | n-C₄H₉ | CH₃ | 4-F(Ph) |
| 1.90 | n-C₄H₉ | CH₃ | 4-OCH₃(Ph) |
| 1.91 | n-C₄H₉ | CH₃ | 4-CH₃(Ph) |
| 1.92 | n-C₄H₉ | CH₃ | 4-NO₂(Ph) |
| 1.93 | n-C₄H₉ | CH₃ | 2,4-Cl(Ph) |
| 1.94 | n-C₄H₉ | CH₃ | 2,4-F(Ph) |
| 1.95 | iso-C₄H₉ | CH₃ | Ph |
| 1.96 | iso-C₄H₉ | CH₃ | 2-Cl(Ph) |
| 1.97 | iso-C₄H₉ | CH₃ | 3-Cl(Ph) |
| 1.98 | iso-C₄H₉ | CH₃ | 4-Cl(Ph) |
| 1.99 | iso-C₄H₉ | CH₃ | 4-F(Ph) |
| 1.100 | iso-C₄H₉ | CH₃ | 2-OCH₃(Ph) |
| 1.101 | iso-C₄H₉ | CH₃ | 3-OCH₃(Ph) |
| 1.102 | iso-C₄H₉ | CH₃ | 4-OCH₃(Ph) |
| 1.103 | iso-C₄H₉ | CH₃ | 4-CH₃(Ph) |
| 1.104 | iso-C₄H₉ | CH₃ | 2,4-Cl(Ph) |
| 1.105 | iso-C₄H₉ | CH₃ | 2,4-F(Ph) |
| 1.106 | cyclopropyl | CH₃ | Ph |
| 1.107 | cyclopropyl | CH₃ | 2-Cl(Ph) |
| 1.108 | cyclopropyl | CH₃ | 3-Cl(Ph) |
| 1.109 | cyclopropyl | CH₃ | 4-Cl(Ph) |
| 1.110 | cyclopropyl | CH₃ | 4-F(Ph) |
| 1.111 | cyclopropyl | CH₃ | 3-OCH₃(Ph) |
| 1.112 | cyclopropyl | CH₃ | 4-OCH₃(Ph) |
| 1.113 | cyclopropyl | CH₃ | 4-CH₃(Ph) |
| 1.114 | cyclopropyl | CH₃ | 4-NO₂(Ph) |
| 1.115 | cyclopropyl | CH₃ | 2,4-Cl(Ph) |
| 1.116 | cyclopropyl | CH₃ | 2,4-F(Ph) |
| 1.117 | 1-CH₃-cyclopropyl | CH₃ | Ph |
| 1.118 | 1-CH₃-cyclopropyl | CH₃ | 2-Cl(Ph) |
| 1.119 | 1-CH₃-cyclopropyl | CH₃ | 3-Cl(Ph) |
| 1.120 | 1-CH₃-cyclopropyl | CH₃ | 4-Cl(Ph) |
| 1.121 | 1-CH₃-cyclopropyl | CH₃ | 2-Br(Ph) |
| 1.122 | CN | CH₃ | Ph |
| 1.123 | CN | CH₃ | 2-Cl(Ph) |
| 1.124 | CN | CH₃ | 3-Cl(Ph) |
| 1.125 | CN | CH₃ | 4-Cl(Ph) |
| 1.126 | CN | CH₃ | 2-Br(Ph) |
| 1.127 | CN | CH₃ | 3-Br(Ph) |
| 1.128 | CN | CH₃ | 4-Br(Ph) |
| 1.129 | CN | CH₃ | 2-F(Ph) |
| 1.130 | CN | CH₃ | 3-F(Ph) |
| 1.131 | CN | CH₃ | 4-F(Ph) |
| 1.132 | CN | CH₃ | 2-OCH₃(Ph) |
| 1.133 | CN | CH₃ | 3-OCH₃(Ph) |
| 1.134 | CN | CH₃ | 4-OCH₃(Ph) |
| 1.135 | CN | CH₃ | 2-CH₃(Ph) |
| 1.136 | CN | CH₃ | 3-CH₃(Ph) |
| 1.137 | CN | CH₃ | 4-CH₃(Ph) |
| 1.138 | CN | CH₃ | 2-CF₃(Ph) |
| 1.139 | CN | CH₃ | 3-CF₃(Ph) |
| 1.140 | CN | CH₃ | 4-CF₃(Ph) |
| 1.141 | CN | CH₃ | 2-NO₂(Ph) |
| 1.142 | CN | CH₃ | 3-NO₂(Ph) |
| 1.143 | CN | CH₃ | 4-NO₂(Ph) |
| 1.144 | CN | CH₃ | 2,3-Cl(Ph) |
| 1.145 | CN | CH₃ | 2,4-Cl(Ph) |
| 1.146 | CN | CH₃ | 2,5-Cl(Ph) |
| 1.147 | CN | CH₃ | 3,4-Cl(Ph) |
| 1.148 | CN | CH₃ | 3,5-Cl(Ph) |
| 1.149 | CN | CH₃ | 2,3,5-Cl(Ph) |
| 1.150 | CN | CH₃ | 2,4,5-Cl(Ph) |
| 1.151 | CN | CH₃ | 3,4,5-Cl(Ph) |
| 1.152 | CN | CH₃ | 2,3-F(Ph) |
| 1.153 | CN | CH₃ | 2,4-F(Ph) |
| 1.154 | CN | CH₃ | 2,5-F(Ph) |
| 1.155 | CN | CH₃ | 3,4-F(Ph) |
| 1.156 | CN | CH₃ | 3,5-F(Ph) |
| 1.157 | CN | CH₃ | 2,3,5-F(Ph) |
| 1.158 | CN | CH₃ | 2,4,5-F(Ph) |
| 1.159 | CN | CH₃ | 3,4,5-F(Ph) |
| 1.160 | CF₃ | CH₃ | Ph |
| 1.161 | CF₃ | CH₃ | 2-Cl(Ph) |
| 1.162 | CF₃ | CH₃ | 3-Cl(Ph) |
| 1.163 | CF₃ | CH₃ | 4-Cl(Ph) |
| 1.164 | CF₃ | CH₃ | 4-F(Ph) |
| 1.165 | CF₃ | CH₃ | 4-CH₃(Ph) |
| 1.166 | CH₃ | C₂H₅ | Ph |
| 1.167 | CH₃ | C₂H₅ | 2-Cl(Ph) |
| 1.168 | CH₃ | C₂H₅ | 3-Cl(Ph) |
| 1.169 | CH₃ | C₂H₅ | 4-Cl(Ph) |
| 1.170 | CH₃ | C₂H₅ | 4-F(Ph) |
| 1.171 | CH₃ | C₂H₅ | 2-OCH₃(Ph) |
| 1.172 | CH₃ | C₂H₅ | 3-OCH₃(Ph) |
| 1.173 | CH₃ | C₂H₅ | 4-OCH₃(Ph) |
| 1.174 | CH₃ | C₂H₅ | 4-CH₃(Ph) |
| 1.175 | CH₃ | C₂H₅ | 4-NO₂(Ph) |
| 1.176 | CH₃ | C₂H₅ | 2,4-Cl(Ph) |
| 1.177 | CH₃ | C₂H₅ | 2,4-F(Ph) |
| 1.178 | CH₃ | n-C₃H₇ | Ph |
| 1.179 | CH₃ | n-C₃H₇ | 2-Cl(Ph) |
| 1.180 | CH₃ | n-C₃H₇ | 3-Cl(Ph) |
| 1.181 | CH₃ | n-C₃H₇ | 4-Cl(Ph) |
| 1.182 | CH₃ | n-C₃H₇ | 4-F(Ph) |
| 1.183 | CH₃ | n-C₃H₇ | 3-OCH₃(Ph) |
| 1.184 | CH₃ | n-C₃H₇ | 4-OCH₃(Ph) |
| 1.185 | CH₃ | n-C₃H₇ | 4-CH₃(Ph) |
| 1.186 | CH₃ | n-C₃H₇ | 4-NO₂(Ph) |
| 1.187 | CH₃ | n-C₃H₇ | 2,4-Cl(Ph) |
| 1.188 | CH₃ | n-C₃H₇ | 2,4-F(Ph) |
| 1.189 | CH₃ | iso-C₃H₇ | Ph |
| 1.190 | CH₃ | iso-C₃H₇ | 4-Cl(Ph) |
| 1.191 | CH₃ | n-C₄H₉ | Ph |
| 1.192 | CH₃ | n-C₄H₉ | 4-Cl(Ph) |
| 1.193 | CH₃ | iso-C₄H₉ | Ph |
| 1.194 | CH₃ | iso-C₄H₉ | 4-Cl(Ph) |
| 1.195 | CN | C₂H₅ | Ph |
| 1.196 | CN | n-C₃H₇ | Ph |
| 1.197 | CN | iso-C₃H₇ | Ph |
| 1.198 | CN | n-C₄H₉ | Ph |
| 1.199 | CN | iso-C₄H₉ | Ph |
| 1.200 | CF₃ | C₂H₅ | Ph |
| 1.201 | CF₃ | n-C₃H₇ | Ph |
| 1.202 | CF₃ | iso-C₃H₇ | Ph |
| 1.203 | CF₃ | n-C₄H₉ | Ph |
| 1.204 | CF₃ | iso-C₄H₉ | Ph |
| 1.205 | H | CF₃ | Ph |
| 1.206 | CH₃ | CF₃ | Ph |
| 1.207 | CN | CF₃ | Ph |
| 1.208 | CF₃ | CF₃ | Ph |
| 1.209 | H | CH₂=CH | Ph |
| 1.210 | CH₃ | CH₂=CH | Ph |
| 1.211 | CN | CH₂=CH | Ph |
| 1.212 | CF₃ | CH₂=CH | Ph |
| 1.213 | H | CH₃CH=CH | Ph |
| 1.214 | CH₃ | CH₃CH=CH | Ph |
| 1.215 | CN | CH₃CH=CH | Ph |

TABLE 1-continued

| Compd # | $R_2$ | $R_6$ | $R_7$ |
|---|---|---|---|
| 1.216 | $CF_3$ | $CH_3CH=CH$ | Ph |
| 1.217 | H | $CH_3$ | $PhCH_2$ |
| 1.218 | H | $CH_3$ | $4\text{-Cl(Ph)}CH_2$ |
| 1.219 | H | $CH_3$ | $4\text{-Br(Ph)}CH_2$ |
| 1.220 | H | $CH_3$ | $4\text{-F(Ph)}CH_2$ |
| 1.221 | H | $CH_3$ | $4\text{-OCH}_3\text{(Ph)}CH_2$ |
| 1.222 | H | $CH_3$ | $4\text{-CF}_3\text{(Ph)}CH_2$ |
| 1.223 | H | $CH_3$ | $4\text{-NO}_2\text{(Ph)}CH_2$ |
| 1.224 | H | $CH_3$ | $2,4\text{-Cl(Ph)}CH_2$ |
| 1.225 | H | $CH_3$ | $2,4\text{-F(Ph)}CH_2$ |
| 1.226 | H | $CH_3$ | $3,4\text{-F(Ph)}CH_2$ |
| 1.227 | $CH_3$ | $CH_3$ | $PhCH_2$ |
| 1.228 | $CH_3$ | $CH_3$ | $2\text{-Cl(Ph)}CH_2$ |
| 1.229 | $CH_3$ | $CH_3$ | $3\text{-Cl(Ph)}CH_2$ |
| 1.230 | $CH_3$ | $CH_3$ | $4\text{-Cl(Ph)}CH_2$ |
| 1.231 | $CH_3$ | $CH_3$ | $2\text{-Br(Ph)}CH_2$ |
| 1.232 | $CH_3$ | $CH_3$ | $3\text{-Br(Ph)}CH_2$ |
| 1.233 | $CH_3$ | $CH_3$ | $4\text{-Br(Ph)}CH_2$ |
| 1.234 | $CH_3$ | $CH_3$ | $2\text{-F(Ph)}CH_2$ |
| 1.235 | $CH_3$ | $CH_3$ | $3\text{-F(Ph)}CH_2$ |
| 1.236 | $CH_3$ | $CH_3$ | $4\text{-F(Ph)}CH_2$ |
| 1.237 | $CH_3$ | $CH_3$ | $2,3\text{-Cl(Ph)}CH_2$ |
| 1.238 | $CH_3$ | $CH_3$ | $2,4\text{-Cl(Ph)}CH_2$ |
| 1.239 | $CH_3$ | $CH_3$ | $2,5\text{-Cl(Ph)}CH_2$ |
| 1.240 | $CH_3$ | $CH_3$ | $3,4\text{-Cl(Ph)}CH_2$ |
| 1.241 | $CH_3$ | $CH_3$ | $3,5\text{-Cl(Ph)}CH_2$ |
| 1.242 | $CH_3$ | $CH_3$ | $2,3,5\text{-Cl(Ph)}CH_2$ |
| 1.243 | $CH_3$ | $CH_3$ | $2,4,5\text{-Cl(Ph)}CH_2$ |
| 1.244 | $CH_3$ | $CH_3$ | $3,4,5\text{-Cl(Ph)}CH_2$ |
| 1.245 | $CH_3$ | $CH_3$ | $2,3\text{-F(Ph)}CH_2$ |
| 1.246 | $CH_3$ | $CH_3$ | $2,4\text{-F(Ph)}CH_2$ |
| 1.247 | $CH_3$ | $CH_3$ | $2,5\text{-F(Ph)}CH_2$ |
| 1.248 | $CH_3$ | $CH_3$ | $3,4\text{-F(Ph)}CH_2$ |
| 1.249 | $CH_3$ | $CH_3$ | $3,5\text{-F(Ph)}CH_2$ |
| 1.250 | $CH_3$ | $CH_3$ | $2,3,5\text{-F(Ph)}CH_2$ |
| 1.251 | $CH_3$ | $CH_3$ | $2,4,5\text{-F(Ph)}CH_2$ |
| 1.252 | $CH_3$ | $CH_3$ | $3,4,5\text{-F(Ph)}CH_2$ |
| 1.253 | $CH_3$ | $C_2H_5$ | $PhCH_2$ |
| 1.254 | $CH_3$ | $n\text{-}C_3H_7$ | $PhCH_2$ |
| 1.255 | $CH_3$ | $iso\text{-}C_3H_7$ | $PhCH_2$ |
| 1.256 | $CH_3$ | $n\text{-}C_4H_9$ | $PhCH_2$ |
| 1.257 | $CH_3$ | $iso\text{-}C_4H_9$ | $PhCH_2$ |
| 1.258 | CN | $C_2H_5$ | $PhCH_2$ |
| 1.259 | CN | $n\text{-}C_3H_7$ | $PhCH_2$ |
| 1.260 | CN | $iso\text{-}C_3H_7$ | $PhCH_2$ |
| 1.261 | CN | $n\text{-}C_4H_9$ | $PhCH_2$ |
| 1.262 | CN | $iso\text{-}C_4H_9$ | $PhCH_2$ |
| 1.263 | $CF_3$ | $C_2H_5$ | $PhCH_2$ |
| 1.264 | $CF_3$ | $iso\text{-}C_3H_7$ | $PhCH_2$ |
| 1.265 | $CF_3$ | $n\text{-}C_3H_7$ | $PhCH_2$ |
| 1.266 | $CF_3$ | $n\text{-}C_4H_9$ | $PhCH_2$ |
| 1.267 | $CF_3$ | $iso\text{-}C_4H_9$ | $PhCH_2$ |
| 1.268 | $CH_3$ | $CH_3$ | $4\text{-Cl(Ph)}CH_2$ |
| 1.269 | $CH_3$ | $C_2H_5$ | $4\text{-Cl(Ph)}CH_2$ |
| 1.270 | $CH_3$ | $n\text{-}C_3H_7$ | $4\text{-Cl(Ph)}CH_2$ |
| 1.271 | $CH_3$ | $iso\text{-}C_3H_7$ | $4\text{-Cl(Ph)}CH_2$ |
| 1.272 | $CH_3$ | $n\text{-}C_4H_9$ | $4\text{-Cl(Ph)}CH_2$ |
| 1.273 | $CH_3$ | $iso\text{-}C_4H_9$ | $4\text{-Cl(Ph)}CH_2$ |
| 1.274 | $CH_3$ | cyclopropyl | $4\text{-Cl(Ph)}CH_2$ |
| 1.275 | CN | cyclopropyl | $4\text{-Cl(Ph)}CH_2$ |
| 1.276 | $CF_3$ | cyclopropyl | $4\text{-Cl(Ph)}CH_2$ |
| 1.277 | H | $CH_2=CH$ | $4\text{-Cl(Ph)}CH_2$ |
| 1.278 | $CH_3$ | $CH_2=CH$ | $4\text{-Cl(Ph)}CH_2$ |
| 1.279 | CN | $CH_2=CH$ | $4\text{-Cl(Ph)}CH_2$ |
| 1.280 | $CF_3$ | $CH_2=CH$ | $4\text{-Cl(Ph)}CH_2$ |
| 1.281 | H | $CH_3CH=CH$ | $4\text{-Cl(Ph)}CH_2$ |
| 1.282 | $CH_3$ | $CH_3CH=CH$ | $4\text{-Cl(Ph)}CH_2$ |
| 1.283 | CN | $CH_3CH=CH$ | $4\text{-Cl(Ph)}CH_2$ |
| 1.284 | $CF_3$ | $CH_3CH=CH$ | $4\text{-Cl(Ph)}CH_2$ |
| 1.285 | $CH_3$ | $CH_3$ | $2,4\text{-Cl(Ph)}CH_2$ |
| 1.286 | $CH_3$ | $C_2H_5$ | $2,4\text{-Cl(Ph)}CH_2$ |
| 1.287 | $CH_3$ | $n\text{-}C_3H_7$ | $2,4\text{-Cl(Ph)}CH_2$ |
| 1.288 | $CH_3$ | $iso\text{-}C_3H_7$ | $2,4\text{-Cl(Ph)}CH_2$ |
| 1.289 | $CH_3$ | $n\text{-}C_4H_9$ | $2,4\text{-Cl(Ph)}CH_2$ |
| 1.290 | $CF_3$ | $iso\text{-}C_4H_9$ | $2,4\text{-Cl(Ph)}CH_2$ |
| 1.291 | $CH_3$ | $CH_2=CH$ | $2,4\text{-Cl(Ph)}CH_2$ |
| 1.288 | $CH_3$ | $CH_3CH=CH$ | $2,4\text{-Cl(Ph)}CH_2$ |
| 1.289 | CN | $CH_3CH=CH$ | $2,4\text{-Cl(Ph)}CH_2$ |
| 1.290 | $CF_3$ | $CH_3CH=CH$ | $2,4\text{-Cl(Ph)}CH_2$ |
| 1.291 | H | $CH_3$ | $PhCH_2CH_2$ |
| 1.288 | $CH_3$ | $CH_3$ | $PhCH_2CH_2$ |
| 1.289 | $CH_3$ | $C_2H_5$ | $PhCH_2CH_2$ |
| 1.290 | $CH_3$ | $n\text{-}C_3H_7$ | $PhCH_2CH_2$ |
| 1.291 | $CH_3$ | $iso\text{-}C_3H_7$ | $PhCH_2CH_2$ |
| 1.292 | $CH_3$ | $n\text{-}C_4H_9$ | $PhCH_2CH_2$ |
| 1.293 | $CH_3$ | $iso\text{-}C_4H_9$ | $PhCH_2CH_2$ |
| 1.294 | $CH_3$ | $CH_2=CH$ | $PhCH_2CH_2$ |
| 1.295 | $CH_3$ | $CH_3CH=CH$ | $PhCH_2CH_2$ |
| 1.296 | CN | $CH_3$ | $PhCH_2CH_2$ |
| 1.297 | CN | $C_2H_5$ | $PhCH_2CH_2$ |
| 1.298 | CN | $n\text{-}C_3H_7$ | $PhCH_2CH_2$ |
| 1.299 | CN | $iso\text{-}C_3H_7$ | $PhCH_2CH_2$ |
| 1.300 | $CF_3$ | $CH_3$ | $PhCH_2CH_2$ |
| 1.301 | $CF_3$ | $C_2H_5$ | $PhCH_2CH_2$ |
| 1.302 | $CF_3$ | $n\text{-}C_3H_7$ | $PhCH_2CH_2$ |
| 1.303 | $CF_3$ | $iso\text{-}C_3H_7$ | $PhCH_2CH_2$ |
| 1.304 | $CF_3$ | $n\text{-}C_4H_9$ | $PhCH_2CH_2$ |
| 1.305 | $CF_3$ | $iso\text{-}C_4H_9$ | $PhCH_2CH_2$ |
| 1.306 | $CF_3$ | $CH_2=CH$ | $PhCH_2CH_2$ |
| 1.307 | $CF_3$ | $CH_3CH=CH$ | $PhCH_2CH_2$ |
| 1.308 | cyclopropyl | $CH_3$ | $PhCH_2CH_2$ |
| 1.309 | cyclopropyl | $C_2H_5$ | $PhCH_2CH_2$ |
| 1.310 | cyclopropyl | $n\text{-}C_3H_7$ | $PhCH_2CH_2$ |
| 1.311 | cyclopropyl | $iso\text{-}C_3H_7$ | $PhCH_2CH_2$ |
| 1.312 | cyclopropyl | $n\text{-}C_4H_9$ | $PhCH_2CH_2$ |
| 1.313 | cyclopropyl | $iso\text{-}C_4H_9$ | $PhCH_2CH_2$ |
| 1.314 | cyclopropyl | $CH_2=CH$ | $PhCH_2CH_2$ |
| 1.315 | cyclopropyl | $CH_3CH=CH$ | $PhCH_2CH_2$ |
| 1.316 | H | $CH_3$ | $PhCH_2CH_2CH_2$ |
| 1.317 | $CH_3$ | $CH_3$ | $PhCH_2CH_2CH_2$ |
| 1.318 | $CH_3$ | $C_2H_5$ | $PhCH_2CH_2CH_2$ |
| 1.319 | $CH_3$ | $n\text{-}C_3H_7$ | $PhCH_2CH_2CH_2$ |
| 1.320 | $CH_3$ | $iso\text{-}C_3H_7$ | $PhCH_2CH_2CH_2$ |
| 1.321 | $CH_3$ | $n\text{-}C_4H_9$ | $PhCH_2CH_2CH_2$ |
| 1.322 | $CH_3$ | $iso\text{-}C_4H_9$ | $PhCH_2CH_2CH_2$ |
| 1.323 | $CH_3$ | $CH_2=CH$ | $PhCH_2CH_2CH_2$ |
| 1.324 | $CH_3$ | $CH_3CH=CH$ | $PhCH_2CH_2CH_2$ |
| 1.325 | CN | $CH_3$ | $PhCH_2CH_2CH_2$ |
| 1.326 | CN | $C_2H_5$ | $PhCH_2CH_2CH_2$ |
| 1.327 | CN | $n\text{-}C_3H_7$ | $PhCH_2CH_2CH_2$ |
| 1.328 | CN | $iso\text{-}C_3H_7$ | $PhCH_2CH_2CH_2$ |
| 1.329 | CN | $n\text{-}C_4H_9$ | $PhCH_2CH_2CH_2$ |
| 1.330 | CN | $iso\text{-}C_4H_9$ | $PhCH_2CH_2CH_2$ |
| 1.331 | CN | $CH_2=CH$ | $PhCH_2CH_2CH_2$ |
| 1.332 | CN | $CH_3CH=CH$ | $PhCH_2CH_2CH_2$ |
| 1.333 | $CF_3$ | $CH_3$ | $PhCH_2CH_2CH_2$ |
| 1.334 | $CF_3$ | $C_2H_5$ | $PhCH_2CH_2CH_2$ |
| 1.335 | $CF_3$ | $n\text{-}C_3H_7$ | $PhCH_2CH_2CH_2$ |
| 1.336 | $CF_3$ | $iso\text{-}C_3H_7$ | $PhCH_2CH_2CH_2$ |
| 1.337 | $CF_3$ | $n\text{-}C_4H_9$ | $PhCH_2CH_2CH_2$ |
| 1.338 | $CF_3$ | $iso\text{-}C_4H_9$ | $PhCH_2CH_2CH_2$ |
| 1.339 | $CF_3$ | $CH_2=CH$ | $PhCH_2CH_2CH_2$ |
| 1.340 | $CF_3$ | $CH_3CH=CH$ | $PhCH_2CH_2CH_2$ |

Table 2: Compounds 2.1 to 2.340 are compounds of Formula I wherein A, $R_3$, $R_4$, and $R_5$ are hydrogen; X is N and Z is O; $R_1$ is methyl; and $R_2$, $R_6$, and $R_7$ are defined as in Table 1. Compounds 2.11 (oil) and 2.14A (oil).

Table 3: Compounds 3.1 to 3.340 are compounds of Formula I wherein A, $R_3$, $R_4$, and $R_5$ are hydrogen; X is N and Z is NH, $R_1$ is methyl; and $R_2$, $R_6$, and $R_7$ are defined as in Table 1. Compounds 3.11 (oil, 4:1 A:B isomers) and 3.14A (oil, 7:3 cis:trans cyclopropane isomers).

Typical compounds of Formula I encompassed by the present invention wherein A, $R_3$, $R_4$, and $R_5$ are hydrogen; X is CH and Z is O; and $R_1$ is methyl include those compounds presented in Table 4 of Formula III where $R_2$, $R_6$, and $R_7$ are defined in Table 4.

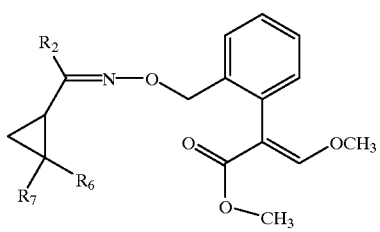

Formula III

TABLE 4

| Compd # | $R_2$ | $R_6$ | $R_7$ |
|---|---|---|---|
| 4.1 | H | $CH_3$ | 2-pyridyl |
| 4.2 | H | $CH_3$ | 3-pyridyl |
| 4.3 | H | $CH_3$ | 4-pyridyl |
| 4.4 | H | $CH_3$ | 2-pyrazinyl |
| 4.5 | H | $CH_3$ | 4-pyrimidinyl |
| 4.6 | H | $CH_3$ | 5-pyrimidinyl |
| 4.7 | H | $CH_3$ | 3-pyridazinyl |
| 4.8 | H | $CH_3$ | 4-pyridazinyl |
| 4.9 | H | $CH_3$ | 2-furyl |
| 4.10 | H | $CH_3$ | 3-furyl |
| 4.11 | H | $CH_3$ | 2-thienyl |
| 4.12 | H | $CH_3$ | 3-thienyl |
| 4.13 | $CH_3$ | $CH_3$ | 2-pyridyl |
| 4.14 | $CH_3$ | $CH_3$ | 3-pyridyl |
| 4.15 | $CH_3$ | $CH_3$ | 4-pyridyl |
| 4.16 | $CH_3$ | $CH_3$ | 2-pyrazinyl |
| 4.17 | $CH_3$ | $CH_3$ | 4-pyrimidinyl |
| 4.18 | $CH_3$ | $CH_3$ | 5-pyrimidinyl |
| 4.19 | $CH_3$ | $CH_3$ | 3-pyridazinyl |
| 4.20 | $CH_3$ | $CH_3$ | 4-pyridazinyl |
| 4.21 | $CH_3$ | $CH_3$ | 2-furyl |
| 4.22 | $CH_3$ | $CH_3$ | 3-furyl |
| 4.23 | $CH_3$ | $CH_3$ | 2-thienyl |
| 4.24 | $CH_3$ | $CH_3$ | 3-thienyl |
| 4.25 | $CH_3$ | $CH_3$ | 1-$CH_3$-3-(1H)- |
| 4.26 | $CH_3$ | $CH_3$ | 1-$CH_3$-4-(1H)- |
| 4.27 | $CH_3$ | $CH_3$ | 5-(1H)-pyrazolyl |
| 4.28 | $CH_3$ | $CH_3$ | 4-(1H)-imidazolyl |
| 4.29 | $CH_3$ | $CH_3$ | 5-(1H)-imidazolyl |
| 4.30 | $CH_3$ | $CH_3$ | 5-(1H)-pyrazolyl |
| 4.31 | $CH_3$ | $CH_3$ | 3-isothiazolyl |
| 4.32 | $CH_3$ | $CH_3$ | 4-isothiazolyl |
| 4.33 | $CH_3$ | $CH_3$ | 5-isothiazolyl |
| 4.34 | $CH_3$ | $CH_3$ | 4-thiazolyl |
| 4.35 | $CH_3$ | $CH_3$ | 5-thiazolyl |
| 4.36 | $CH_3$ | $CH_3$ | 3-isooxazolyl |
| 4.37 | $CH_3$ | $CH_3$ | 4-isooxazolyl |
| 4.38 | $CH_3$ | $CH_3$ | 5-isooxazolyl |
| 4.39 | $CH_3$ | $CH_3$ | 4-oxazolyl |
| 4.40 | $CH_3$ | $CH_3$ | 5-oxazolyl |
| 4.41 | $CH_3$ | $CH_3$ | 1-methyl-2-(1H)- |
| 4.42 | $CH_3$ | $CH_3$ | 1-methyl-3-(1H)- |
| 4.43 | $CH_3$ | $CH_3$ | 2-quinolinyl |
| 4.44 | $CH_3$ | $CH_3$ | 3-quinolinyl |
| 4.45 | $CH_3$ | $CH_3$ | 4-quinolinyl |
| 4.46 | $CH_3$ | $CH_3$ | 3-Cl-pyrid-2-yl |
| 4.47 | $CH_3$ | $CH_3$ | 2-Cl-pyrid-3-yl |
| 4.48 | $CH_3$ | $CH_3$ | 2-Cl-pyrid-4-yl |
| 4.49 | $CH_3$ | $CH_3$ | 4-Cl-furan-2-yl |
| 4.50 | $CH_3$ | $CH_3$ | 2-Cl-furan-3-yl |
| 4.51 | $C_2H_3$ | $CH_3$ | 2-pyridyl |
| 4.52 | $C_2H_3$ | $CH_3$ | 3-pyridyl |
| 4.53 | $C_2H_3$ | $CH_3$ | 4-pyridyl |
| 4.54 | $C_2H_3$ | $CH_3$ | 2-furyl |
| 4.55 | $C_2H_3$ | $CH_3$ | 3-furyl |
| 4.56 | $C_2H_3$ | $CH_3$ | 2-thienyl |
| 4.57 | $C_2H_3$ | $CH_3$ | 3-thienyl |
| 4.58 | n-$C_3H_7$ | $CH_3$ | 2-pyridyl |
| 4.59 | n-$C_3H_7$ | $CH_3$ | 3-pyridyl |
| 4.60 | n-$C_3H_7$ | $CH_3$ | 4-pyridyl |
| 4.61 | n-$C_3H_7$ | $CH_3$ | 2-furyl |
| 4.62 | n-$C_3H_7$ | $CH_3$ | 3-furyl |
| 4.63 | n-$C_3H_7$ | $CH_3$ | 2-thienyl |
| 4.64 | n-$C_3H_7$ | $CH_3$ | 3-thienyl |
| 4.65 | iso-$C_3H_7$ | $CH_3$ | 2-pyridyl |
| 4.66 | iso-$C_3H_7$ | $CH_3$ | 3-pyridyl |
| 4.67 | iso-$C_3H_7$ | $CH_3$ | 4-pyridyl |
| 4.68 | iso-$C_3H_7$ | $CH_3$ | 2-furyl |
| 4.69 | iso-$C_3H_7$ | $CH_3$ | 3-furyl |
| 4.70 | iso-$C_3H_7$ | $CH_3$ | 2-thienyl |
| 4.71 | iso-$C_3H_7$ | $CH_3$ | 3-thienyl |
| 4.72 | n-$C_4H_9$ | $CH_3$ | 2-pyridyl |
| 4.73 | n-$C_4H_9$ | $CH_3$ | 3-pyridyl |
| 4.74 | n-$C_4H_9$ | $CH_3$ | 4-pyridyl |
| 4.75 | n-$C_4H_9$ | $CH_3$ | 2-furyl |
| 4.76 | n-$C_4H_9$ | $CH_3$ | 3-furyl |
| 4.77 | n-$C_4H_9$ | $CH_3$ | 2-thienyl |
| 4.78 | n-$C_4H_9$ | $CH_3$ | 3-thienyl |
| 4.79 | iso-$C_4H_9$ | $CH_3$ | 2-pyridyl |
| 4.80 | iso-$C_4H_9$ | $CH_3$ | 3-pyridyl |
| 4.81 | iso-$C_4H_9$ | $CH_3$ | 4-pyridyl |
| 4.82 | iso-$C_4H_9$ | $CH_3$ | 2-furyl |
| 4.83 | iso-$C_4H_9$ | $CH_3$ | 3-furyl |
| 4.84 | iso-$C_4H_9$ | $CH_3$ | 2-thienyl |
| 4.85 | iso-$C_4H_9$ | $CH_3$ | 3-thienyl |
| 4.86 | c-$C_3H_5$ | $CH_3$ | 2-pyridyl |
| 4.87 | c-$C_3H_5$ | $CH_3$ | 3-pyridyl |
| 4.88 | c-$C_3H_5$ | $CH_3$ | 4-pyridyl |
| 4.89 | c-$C_3H_5$ | $CH_3$ | 2-furyl |
| 4.90 | c-$C_3H_5$ | $CH_3$ | 3-furyl |
| 4.91 | c-$C_3H_5$ | $CH_3$ | 2-thienyl |
| 4.92 | c-$C_3H_5$ | $CH_3$ | 3-thienyl |
| 4.93 | CN | $CH_3$ | 2-pyridyl |
| 4.94 | CN | $CH_3$ | 3-pyridyl |
| 4.95 | CN | $CH_3$ | 4-pyridyl |
| 4.96 | CN | $CH_3$ | 2-furyl |
| 4.97 | CN | $CH_3$ | 3-furyl |
| 4.98 | CN | $CH_3$ | 2-thienyl |
| 4.99 | CN | $CH_3$ | 3-thienyl |
| 4.100 | $CF_3$ | $CH_3$ | 2-pyridyl |
| 4.101 | $CF_3$ | $CH_3$ | 3-pyridyl |
| 4.102 | $CF_3$ | $CH_3$ | 4-pyridyl |
| 4.104 | $CF_3$ | $CH_3$ | 2-thienyl |
| 4.105 | $CF_3$ | $CH_3$ | 2-thienyl |
| 4.106 | $CF_3$ | $CH_3$ | 3-thienyl |
| 4.107 | $CH_3$ | $C_2H_5$ | 2-pyridyl |
| 4.108 | $CH_3$ | $C_2H_5$ | 3-pyridyl |
| 4.109 | $CH_3$ | $C_2H_5$ | 4-pyridyl |
| 4.110 | $CH_3$ | $C_2H_5$ | 2-furyl |
| 4.111 | $CH_3$ | $C_2H_5$ | 3-furyl |
| 4.112 | $CH_3$ | $C_2H_5$ | 2-thienyl |
| 4.113 | $CH_3$ | $C_2H_5$ | 3-thienyl |
| 4.114 | $CH_3$ | n-$C_3H_7$ | 2-pyridyl |
| 4.115 | $CH_3$ | n-$C_3H_7$ | 3-pyridyl |
| 4.116 | $CH_3$ | n-$C_3H_7$ | 4-pyridyl |
| 4.117 | $CH_3$ | n-$C_3H_7$ | 2-furyl |
| 4.118 | $CH_3$ | n-$C_3H_7$ | 3-furyl |
| 4.119 | $CH_3$ | n-$C_4H_9$ | 2-pyridyl |
| 4.120 | $CH_3$ | n-$C_4H_9$ | 3-pyridyl |
| 4.121 | $CH_3$ | n-$C_4H_9$ | 4-pyridyl |
| 4.122 | $CH_3$ | n-$C_4H_9$ | 2-thienyl |
| 4.123 | $CH_3$ | n-$C_4H_9$ | 3-thienyl |
| 4.124 | $CH_3$ | iso-$C_4H_9$ | 2-pyridyl |
| 4.125 | $CH_3$ | iso-$C_4H_9$ | 3-pyridyl |
| 4.126 | $CH_3$ | iso-$C_4H_9$ | 4-pyridyl |
| 4.127 | $CH_3$ | iso-$C_4H_9$ | 2-thienyl |
| 4.128 | $CH_3$ | iso-$C_4H_9$ | 3-thienyl |
| 4.129 | $CH_3$ | cyclopropyl | 2-pyridyl |
| 4.130 | $CH_3$ | cyclopropyl | 3-pyridyl |
| 4.131 | $CH_3$ | cyclopropyl | 4-pyridyl |
| 4.132 | $CH_3$ | cyclopropyl | 2-thienyl |
| 4.133 | $CH_3$ | cyclopropyl | 3-thienyl |
| 4.134 | $CF_3$ | $CH_3$ | 2-pyridyl |
| 4.135 | $CF_3$ | $CH_3$ | 3-pyridyl |
| 4.136 | $CF_3$ | $CH_3$ | 4-pyridyl |
| 4.134 | $CF_3$ | $CH_3$ | 2-furyl |
| 4.135 | $CF_3$ | $CH_3$ | 3-furyl |
| 4.136 | $CF_3$ | $CH_3$ | 2-thienyl |
| 4.137 | $CF_3$ | $CH_3$ | 3-thienyl |

TABLE 4-continued

| Compd # | $R_2$ | $R_6$ | $R_7$ |
|---|---|---|---|
| 4.138 | $CF_3$ | $C_2H_5$ | 2-pyridyl |
| 4.139 | $CF_3$ | $C_2H_5$ | 3-pyridyl |
| 4.140 | $CF_3$ | $C_2H_5$ | 4-pyridyl |
| 4.141 | $CF_3$ | $C_2H_5$ | 2-furyl |
| 4.142 | $CF_3$ | $C_2H_5$ | 3-furyl |
| 4.143 | $CF_3$ | $C_2H_5$ | 2-thienyl |
| 4.144 | $CF_3$ | $C_2H_5$ | 3-thienyl |
| 4.145 | CN | $CH_3$ | 2-pyridyl |
| 4.146 | CN | $CH_3$ | 3-pyridyl |
| 4.147 | CN | $CH_3$ | 4-pyridyl |
| 4.148 | CN | $CH_3$ | 2-furyl |
| 4.149 | CN | $CH_3$ | 3-furyl |
| 4.150 | CN | $CH_3$ | 2-thienyl |
| 4.151 | CN | $CH_3$ | 3-thienyl |
| 4.152 | CN | $C_2H_5$ | 2-pyridyl |
| 4.153 | CN | $C_2H_5$ | 3-pyridyl |
| 4.154 | CN | $C_2H_5$ | 4-pyridyl |
| 4.155 | CN | $C_2H_5$ | 2-furyl |
| 4.156 | CN | $C_2H_5$ | 3-furyl |
| 4.157 | CN | $C_2H_5$ | 2-thienyl |
| 4.158 | CN | $C_2H_5$ | 3-thienyl |

Table 5: Compounds 5.1 to 5.158 are compounds of Formula I wherein A, $R_3$, $R_4$, and $R_5$ are hydrogen; X is N and Z is O; $R_1$ is methyl; and $R_2$, $R_6$, and $R_7$ are defined as in Table 4.

Table 6: Compounds 6.1 to 6.158 are compounds of Formula I wherein A, $R_3$, $R_4$, and $R_5$ are hydrogen; X is N and Z is NH, $R_1$ is methyl; and $R_2$, $R_6$, and $R_7$ are defined as in Table 4.

Typical compounds of Formula I encompassed by the present invention wherein A, $R_3$, $R_4$, and $R_5$ are hydrogen; X is CH and Z is O; and $R_1$ is methyl include those compounds presented in Table 7 of Formula III where $R_2$, $R_6$, and $R_7$ are defined in Table 7

Formula III

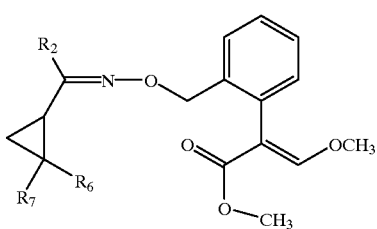

TABLE 7

| Compd # | $R_2$ | $R_6$ | $R_7$ |
|---|---|---|---|
| 7.1 | H | H | 2,6-Cl(Ph) |
| 7.2 | H | H | 2,3,6-Cl(Ph) |
| 7.3 | H | H | 2,4,6-Cl(Ph) |
| 7.4 | H | H | 2,6-Br(Ph) |
| 7.5 | H | H | 2,3,6-Br(Ph) |
| 7.6 | H | H | 2,4,6-Br(Ph) |
| 7.7 | H | H | 2,6-F(Ph) |
| 7.8 | H | H | 2,3,6-F(Ph) |
| 7.9 | H | H | 2,4,6-F(Ph) |
| 7.10 | H | H | 2,6-$CH_3$(Ph) |
| 7.11 | H | H | 2,3,6-$CH_3$(Ph) |
| 7.12 | H | H | 2,4,6-$CH_3$(Ph) |
| 7.13 | H | H | 2,6-$CH_3O$(Ph) |
| 7.14 | H | H | 2,3,6-$CH_3O$(Ph) |
| 7.15 | H | H | 2,4,6-$CH_3O$(Ph) |
| 7.16 | $CH_3$ | H | 2,6-Cl(Ph) |
| 7.17 | $CH_3$ | H | 2,3,6-Cl(Ph) |
| 7.18 | $CH_3$ | H | 2,4,6-Cl(Ph) |
| 7.19 | $CH_3$ | H | 2,6-Br(Ph) |
| 7.20 | $CH_3$ | H | 2,3,6-Br(Ph) |
| 7.21 | $CH_3$ | H | 2,4,6-Br(Ph) |
| 7.22 | $CH_3$ | H | 2,6-F(Ph) |
| 7.23 | $CH_3$ | H | 2,3,6-F(Ph) |
| 7.24 | $CH_3$ | H | 2,4,6-F(Ph) |
| 7.25 | $CH_3$ | H | 2,6-$CH_3$(Ph) |
| 7.26 | $CH_3$ | H | 2,3,6-$CH_3$(Ph) |
| 7.27 | $CH_3$ | H | 2,4,6-$CH_3$(Ph) |
| 7.28 | $CH_3$ | H | 2,6-$CH_3O$(Ph) |
| 7.29 | $CH_3$ | H | 2,3,6-$CH_3O$(Ph) |
| 7.30 | $CH_3$ | H | 2,4,6-$CH_3O$(Ph) |
| 7.31 | $CH_3$ | H | 2,6-$NO_2$(Ph) |
| 7.32 | $CH_3$ | H | 2,6-CN(Ph) |
| 7.33 | $CH_3$ | H | 2,3,6-CN(Ph) |
| 7.34 | $CH_3$ | H | 2,4,6-CN(Ph) |
| 7.35 | $CH_3$ | H | 2,6-Ph(Ph) |
| 7.36 | $CH_3$ | H | 2,3,6-Ph(Ph) |
| 7.37 | $CH_3$ | H | 2,4,6-Ph(Ph) |
| 7.38 | $CH_3$ | H | 2,6-PhO(Ph) |
| 7.39 | $CH_3$ | H | 2,3,6-PhO(Ph) |
| 7.40 | $CH_3$ | H | 2,4,6-PhO(Ph) |
| 7.41 | $CH_3$ | H | 2,6-$CF_3$(Ph) |
| 7.42 | $CH_3$ | H | 2,3,6-$CF_3$(Ph) |
| 7.43 | $CH_3$ | H | 2,4,6-$CF_{3(Ph)}$ |
| 7.44 | $CH_3$ | H | 2,6-$CF_3O$(Ph) |
| 7.45 | $CH_3$ | H | 2,3,6-$CF_3O$(Ph) |
| 7.46 | $CH_3$ | H | 2,4,6-$CF_3O$(Ph) |
| 7.47 | $CH_3$ | H | 2,3,4,6-Cl(Ph) |
| 7.48 | $CH_3$ | H | 2,3,5,6-Cl(Ph) |
| 7.49 | $CH_3$ | H | 2,3,4,5,6-Cl(Ph) |
| 7.50 | $CH_3$ | H | 2,3,4,6-Ph(Ph) |
| 7.51 | $CH_3$ | H | 2,3,5,6-Ph(Ph) |
| 7.52 | $CH_3$ | H | 2,3,4,5,6-Ph(Ph) |
| 7.53 | $CH_3$ | H | 2,3,4,6-PhO(Ph) |
| 7.54 | $CH_3$ | H | 2,3,5,6-PhO(Ph) |
| 7.55 | $CH_3$ | H | 2,3,4,5,6-PhO(Ph) |
| 7.56 | $CH_3$ | H | 2,3,4,6-Br(Ph) |
| 7.57 | $CH_3$ | H | 2,3,5,6-Br(Ph) |
| 7.58 | $CH_3$ | H | 2,3,4,5,6-Br(Ph) |
| 7.59 | $CH_3$ | H | 2,3,4,6-F(Ph) |
| 7.60 | $CH_3$ | H | 2,3,5,6-F(Ph) |
| 7.61 | $CH_3$ | H | 2,3,4,5,6-F(Ph) |
| 7.62 | $CH_3$ | H | 2,3,4,6-$CH_3$(Ph) |
| 7.63 | $CH_3$ | H | 2,3,5,6-$CH_3$(Ph) |
| 7.64 | $CH_3$ | H | 2,3,4,5,6-$CH_3$(Ph) |
| 7.65 | $CH_3$ | H | 2,3,4,6-$C_2H_5$(Ph) |
| 7.66 | $CH_3$ | H | 2,3,5,6-$C_2H_5$(Ph) |
| 7.67 | $CH_3$ | H | 2,3,4,5,6-$C_2H_5$(Ph) |
| 7.68 | $CH_3$ | H | 2,3,4,6-$CH_3O$(Ph) |
| 7.69 | $CH_3$ | H | 2,3,5,6-$CH_3O$(Ph) |
| 7.70 | $CH_3$ | H | 2,3,4,5,6-$CH_3O$(Ph) |
| 7.71 | $CH_3$ | H | 2,3,4,6-$CF_3$(Ph) |
| 7.72 | $CH_3$ | H | 2,3,5,6-$CF_3$(Ph) |
| 7.73 | $CH_3$ | H | 2,3,4,5,6-$CF_3$(Ph) |
| 7.74 | $CH_3$ | H | 2,3,4,6-$CF_3O$(Ph) |
| 7.75 | $CH_3$ | H | 2,3,5,6-$CF_3O$(Ph) |
| 7.76 | $CH_3$ | H | 2,3,4,5,6-$CF_3O$(Ph) |
| 7.77 | $CH_3$ | H | 2,3,4,6-CN(Ph) |
| 7.78 | $CH_3$ | H | 2,3,5,6-CN(Ph) |
| 7.79 | $CH_3$ | H | 2,3,4,5,6-CN(Ph) |
| 7.80 | $CH_3$ | H | 2-Br-6-Cl(Ph) |
| 7.81 | $CH_3$ | H | 2-Br-6-F(Ph) |
| 7.82 | $CH_3$ | H | 2-Br-6-$CH_3$(Ph) |
| 7.83 | $CH_3$ | H | 2-Br-6-$CF_3$(Ph) |
| 7.84 | $CH_3$ | H | 2-Br-6-$CH_3O$(Ph) |
| 7.85 | $CH_3$ | H | 2-Br-6-$CF_3O$(Ph) |
| 7.86 | $CH_3$ | H | 2-Br-6-CN(Ph) |
| 7.87 | $CH_3$ | H | 2-Cl-6-F(Ph) |
| 7.88 | $CH_3$ | H | 2-Cl-6-$CH_3$(Ph) |
| 7.89 | $CH_3$ | H | 2-Cl-6-$CF_3$(Ph) |
| 7.90 | $CH_3$ | H | 2-Cl-6-$CH_3O$(Ph) |
| 7.91 | $CH_3$ | H | 2-Cl-6-$CF_3O$(Ph) |
| 7.92 | $CH_3$ | H | 2-Cl-6-CN(Ph) |
| 7.93 | $CH_3$ | H | 2-F-6-$CH_3$(Ph) |
| 7.94 | $CH_3$ | H | 2-F-6-$CF_3$(Ph) |

TABLE 7-continued

| Compd # | R$_2$ | R$_6$ | R$_7$ |
|---|---|---|---|
| 7.95 | CH$_3$ | H | 2-F-6-CH$_3$O(Ph) |
| 7.96 | CH$_3$ | H | 2-F-6-CF$_3$O(Ph) |
| 7.97 | CH$_3$ | H | 6-CN,2F(Ph) |
| 7.98 | CH$_3$ | H | 2-CH$_3$-6-CF$_3$(Ph) |
| 7.99 | CH$_3$ | H | 6-CH$_3$O-2-CH$_3$(Ph) |
| 7.100 | CH$_3$ | H | 2-CH$_3$-6-CF$_3$O(Ph) |
| 7.101 | CH$_3$ | H | 6-CN-2-OCH$_3$(Ph) |
| 7.102 | CH$_3$ | H | 6-CN-2-CH$_3$(Ph) |
| 7.103 | CH$_3$ | H | 3,6-Cl-2-F(Ph) |
| 7.104 | CH$_3$ | H | 3Cl-2,6-F(Ph) |
| 7.105 | CH$_3$ | H | 4-Cl-2,6-F(Ph) |
| 7.106 | CH$_3$ | H | 2-Br-3,6-Cl(Ph) |
| 7.107 | CH$_3$ | H | 2,3-Br-6-Cl(Ph) |
| 7.108 | CH$_3$ | H | 3-Cl-2,6Br(Ph) |
| 7.109 | CH$_3$ | H | 2,6-Cl-3-F(Ph) |
| 7.110 | CH$_3$ | H | 2,3-Cl-6-F(Ph) |
| 7.111 | CH$_3$ | H | 2-Cl-3,6-F(Ph) |
| 7.112 | CH$_3$ | H | 3-Br-2,6-Cl(Ph) |
| 7.113 | CH$_3$ | H | 3-Br-2,6-F(Ph) |
| 7.114 | CH$_3$ | H | 3-Br-6Cl-2-F(Ph) |
| 7.115 | CH$_3$ | H | 2-Br-5Cl-6-F(Ph) |
| 7.116 | CH$_3$ | H | 2,6-Br-3-F(Ph) |
| 7.117 | CH$_3$ | H | 2,5-Br-6-F(Ph) |
| 7.118 | CH$_3$ | H | 2,4-Cl-6F(Ph) |
| 7.119 | CH$_3$ | H | 2,6-Cl-4F(Ph) |
| 7.120 | CH$_3$ | H | 2,4-Cl-6Br(Ph) |
| 7.121 | CH$_3$ | H | 2,6-Cl-4Br(Ph) |
| 7.122 | CH$_3$ | H | 2,4-F-6-Cl(Ph) |
| 7.123 | CH$_3$ | H | 2,4-F-6-Br(Ph) |
| 7.124 | CH$_3$ | H | 2,6-F-4-Br(Ph) |
| 7.125 | CH$_3$ | H | 2,4-Br-6-F(Ph) |
| 7.126 | CH$_3$ | H | 2,4-Br-6-Cl(Ph) |
| 7.127 | CH$_3$ | H | 2,6-Br-4-Cl(Ph) |
| 7.128 | CH$_3$ | H | 2,6-Br-4-F(Ph) |
| 7.129 | CH$_3$ | H | 2,4-Cl-6-CH$_3$(Ph) |
| 7.130 | CH$_3$ | H | 2,6-Cl-4-CH$_3$(Ph) |
| 7.131 | CH$_3$ | H | 2-Cl-4,6-(CH$_3$)$_2$(Ph) |
| 7.132 | CH$_3$ | H | 4-Cl-2,6-(CH$_3$)$_2$(Ph) |
| 7.133 | CH$_3$ | H | 2,4-F-6-CH$_3$(Ph) |
| 7.134 | CH$_3$ | H | 2,6-F-4-CH$_3$(Ph) |
| 7.135 | CH$_3$ | H | 2-F-4,6-(CH$_3$)$_2$(Ph) |
| 7.136 | CH$_3$ | H | 4-F-2,6-(CH$_3$)$_2$(Ph) |
| 7.137 | CH$_3$ | H | 2,4-Br-6-CH$_3$(Ph) |
| 7.138 | CH$_3$ | H | 2,6-Br-4-CH$_3$(Ph) |
| 7.139 | CH$_3$ | H | 2-Br-4,6-(CH$_3$)$_2$(Ph) |
| 7.140 | CH$_3$ | H | 4-Br-2,6-(CH$_3$)$_2$(Ph) |
| 7.141 | CH$_3$ | H | 2,4-Cl-6-CF$_3$(Ph) |
| 7.142 | CH$_3$ | H | 2,6-Cl-4-CF$_3$(Ph) |
| 7.143 | CH$_3$ | H | 2-Cl-4,6-(CF$_3$)$_2$(Ph) |
| 7.144 | CH$_3$ | H | 4-Cl-2,6-(CF$_3$)$_2$(Ph) |
| 7.145 | CH$_3$ | H | 2,4-F-6-CF$_3$(Ph) |
| 7.146 | CH$_3$ | H | 2,6-F-4-CF$_3$(Ph) |
| 7.147 | CH$_3$ | H | 2-F-3,6-(CF$_3$)$_2$(Ph) |
| 7.148 | CH$_3$ | H | 3-F-2,6-(CF$_3$)$_2$(Ph) |
| 7.149 | CH$_3$ | H | 2,3-Br-6-CF$_3$(Ph) |
| 7.150 | CH$_3$ | H | 2,6-Br-3-CF$_3$(Ph) |
| 7.137 | CH$_3$ | H | 2-Br-4,6-(CF$_3$)$_2$(Ph) |
| 7.138 | CH$_3$ | H | 4-Br-2,6-(CF$_3$)$_2$(Ph) |
| 7.139 | CH$_3$ | H | 2,4-Cl-6-CF$_3$O(Ph) |
| 7.140 | CH$_3$ | H | 2,6-Cl-4-CF$_3$O(Ph) |
| 7.141 | CH$_3$ | H | 2-Cl-4,6-(CF$_3$O)$_2$(Ph) |
| 7.142 | CH$_3$ | H | 4-Cl-2,6-(CF$_3$O)$_2$(Ph) |
| 7.143 | CH$_3$ | H | 2,4-F-6-CF$_3$O(Ph) |
| 7.144 | CH$_3$ | H | 2,6-F-4-CF$_3$O(Ph) |
| 7.145 | CH$_3$ | H | 2-F-4,6-(CF$_3$O)$_2$(Ph) |
| 7.146 | CH$_3$ | H | 4-F-2,6-(CF$_3$O)$_2$(Ph) |
| 7.147 | CH$_3$ | H | 2,4-F-6-CF$_3$O(Ph) |
| 7.148 | CH$_3$ | H | 2,6-F-4-CF$_3$O(Ph) |
| 7.149 | CH$_3$ | H | 2-F-4,6-(CF$_3$O)$_2$(Ph) |
| 7.150 | CH$_3$ | H | 4-F-2,6-(CF$_3$O)$_2$(Ph) |
| 7.151 | CH$_3$ | H | 2-Br-3,4,6-Cl(Ph) |
| 7.152 | CH$_3$ | H | 6-F-2,4,5-Cl(Ph) |
| 7.153 | CH$_3$ | H | 6-Cl-2,4,5-Br(Ph) |
| 7.154 | CH$_3$ | H | 6-F-2,4,5-Br(Ph) |
| 7.155 | CH$_3$ | H | 2-Br-3,4,6-F(Ph) |
| 7.156 | CH$_3$ | H | 2-Cl-3,4,6-F(Ph) |
| 7.157 | CH$_3$ | H | 6-CH$_3$-2,4,5-Cl(Ph) |
| 7.158 | CH$_3$ | H | 6-CH$_3$-2,4,5-Br(Ph) |
| 7.159 | CH$_3$ | H | 6-CH$_3$-2,4,5-F(Ph) |
| 7.160 | CH$_3$ | H | 6-CF$_3$-2,4,5-Cl(Ph) |
| 7.161 | CH$_3$ | H | 6-CF$_3$-2,4,5-Br(Ph) |
| 7.162 | CH$_3$ | H | 6-CF$_3$-2,4,5-F(Ph) |
| 7.163 | CH$_3$ | H | 6-CF$_3$O-2,4,5-Cl(Ph) |
| 7.164 | CH$_3$ | H | 6-CF$_3$O-2,4,5-Br(Ph) |
| 7.165 | CH$_3$ | H | 6-CF$_3$O-2,4,5-F(Ph) |
| 7.166 | CH$_3$ | H | 2-Br-3,5,6-Cl(Ph) |
| 7.167 | CH$_3$ | H | 2-Br-3,5,6-F(Ph) |
| 7.168 | CH$_3$ | H | 2-Cl-3,5,6-F(Ph) |
| 7.169 | CH$_3$ | H | 6-F-2,3,5-Cl(Ph) |
| 7.170 | CH$_3$ | H | 6-Cl-2,3,5-Br(Ph) |
| 7.171 | CH$_3$ | H | 6-F-2,3,5-Br(Ph) |
| 7.172 | CH$_3$ | H | 6-CH$_3$-2,3,5-Cl(Ph) |
| 7.173 | CH$_3$ | H | 6-CH$_3$-2,3,5-Br(Ph) |
| 7.174 | CH$_3$ | H | 2-CH$_3$-3,5,6-F(Ph) |
| 7.175 | CH$_3$ | H | 6-CF$_3$-2,3,5-Cl(Ph) |
| 7.176 | CH$_3$ | H | 6-CF$_3$-2,3,5-Br(Ph) |
| 7.177 | CH$_3$ | H | 2-CF$_3$-3,5,6-F(Ph) |
| 7.178 | CH$_3$ | H | 6-CF$_3$O-2,3,5-Cl(Ph) |
| 7.179 | CH$_3$ | H | 6-CF$_3$O-2,3,5-Br(Ph) |
| 7.180 | CH$_3$ | H | 2-CF$_3$O-3,5,6-F(Ph) |
| 7.172 | CH$_3$ | H | 4-Br-2,3,5,6-Cl(Ph) |
| 7.173 | CH$_3$ | H | 4-F-2,3,5,6-Cl(Ph) |
| 7.174 | CH$_3$ | H | 4-Cl-2,3,5,6-Br(Ph) |
| 7.175 | CH$_3$ | H | 4-F-2,3,5,6-Br(Ph) |
| 7.176 | CH$_3$ | H | 4-Cl-2,3,5,6-F(Ph) |
| 7.177 | CH$_3$ | H | 4-Br-2,3,5,6-F(Ph) |
| 7.178 | CH$_3$ | H | 2-Br-3,4,5,6-Cl(Ph) |
| 7.179 | CH$_3$ | H | 2-F-3,4,5,6-Cl(Ph) |
| 7.180 | CH$_3$ | H | 2-Cl-3,4,5,6-F(Ph) |
| 7.181 | CH$_3$ | H | 2-Br-3,4,5,6-F(Ph) |
| 7.182 | CH$_3$ | H | 6-Cl-2,3,4,5-Br(Ph) |
| 7.183 | CH$_3$ | H | 6-F-2,3,4,5-Br(Ph) |
| 7.184 | CH$_3$ | H | 4-CH$_3$-2,3,5,6-Cl(Ph) |
| 7.185 | CH$_3$ | H | 4-CH$_3$-2,3,5,6-Br(Ph) |
| 7.186 | CH$_3$ | H | 4-CH$_3$-2,3,5,6-F(Ph) |
| 7.187 | CH$_3$ | H | 4-CF$_3$-2,3,5,6-Cl(Ph) |
| 7.188 | CH$_3$ | H | 4-CF$_3$-2,3,5,6-Br(Ph) |
| 7.189 | CH$_3$ | H | 4-CF$_3$-2,3,5,6-F(Ph) |
| 7.190 | CH$_3$ | H | 4-CF$_3$-2,3,5,6-Cl(Ph) |
| 7.191 | CH$_3$ | H | 4-CF$_3$O-2,3,5,6-Br(Ph) |
| 7.192 | CH$_3$ | H | 4-CF$_3$O-2,3,5,6-F(Ph) |
| 7.193 | CH$_3$ | H | 4-CF$_3$O-2,3,5,6-Cl(Ph) |
| 7.194 | CH$_3$ | H | 6-CH$_3$-2,3,4,5-Cl(Ph) |
| 7.195 | CH$_3$ | H | 6-CH$_3$-2,3,4,5-BrPh) |
| 7.196 | CH$_3$ | H | 2-CH$_3$-3,4,5,6-F(Ph) |
| 7.197 | CH$_3$ | H | 6-CF$_3$O-2,3,4,5-Cl(Ph) |
| 7.198 | CH$_3$ | H | 6-CF$_3$O-2,3,4,5-BrPh) |
| 7.199 | CH$_3$ | H | 2-CF$_3$O-3,4,5,6-F(Ph) |
| 7.200 | CH$_3$ | CH$_3$ | 2,6-Cl(Ph) |
| 7.201 | CH$_3$ | CH$_3$ | 2,3,6-Cl(Ph) |
| 7.202 | CH$_3$ | CH$_3$ | 2,4,6-Cl(Ph) |
| 7.203 | CH$_3$ | CH$_3$ | 2,6-Br(Ph) |
| 7.204 | CH$_3$ | CH$_3$ | 2,3,6-Br(Ph) |
| 7.205 | CH$_3$ | CH$_3$ | 2,4,6-Br(Ph) |
| 7.206 | CH$_3$ | CH$_3$ | 2,6-F(Ph) |
| 7.207 | CH$_3$ | CH$_3$ | 2,3,6-F(Ph) |
| 7.208 | CH$_3$ | CH$_3$ | 2,4,6-F(Ph) |
| 7.209 | CH$_3$ | CH$_3$ | 2,6-CH$_3$(Ph) |
| 7.210 | CH$_3$ | CH$_3$ | 2,3,6-CH$_3$(Ph) |
| 7.211 | CH$_3$ | C$_2$H$_5$ | 2,4,6-CH$_3$(Ph) |
| 7.212 | CH$_3$ | n-C$_3$H$_7$ | 2,6-Cl(Ph) |
| 7.213 | CH$_3$ | iso-C$_3$H$_7$ | 2,3,6-Cl(Ph) |
| 7.214 | CH$_3$ | n-C$_4$H$_9$ | 2,4,6-Cl(Ph) |
| 7.215 | CH$_3$ | iso-C$_4$H$_9$ | 2,6-Cl(Ph) |
| 7.216 | CH$_3$ | CH$_2$=CH | 2,3,6-Cl(Ph) |
| 7.217 | CH$_3$ | CH$_3$CH=CH | 2,4,6-Cl(Ph) |
| 7.218 | CN | H | 2,6-Cl(Ph) |
| 7.219 | CN | CH$_3$ | 2,3,6-Cl(Ph) |
| 7.220 | CN | C$_2$H$_5$ | 2,4,6-Cl(Ph) |
| 7.221 | CN | n-C$_3$H$_7$ | 2,6-Cl(Ph) |
| 7.222 | CN | iso-C$_3$H$_7$ | 2,3,6-Cl(Ph) |
| 7.223 | CN | n-C$_4$H$_9$ | 2,4,6-Cl(Ph) |
| 7.224 | CN | iso-C$_4$H$_9$ | 2,6-Cl(Ph) |
| 7.225 | CN | CH$_2$=CH | 2,3,6-Cl(Ph) |

TABLE 7-continued

| Compd # | $R_2$ | $R_6$ | $R_7$ |
|---|---|---|---|
| 7.226 | CN | $CH_3CH=CH$ | 2,4,6-Cl(Ph) |
| 7.227 | $CF_3$ | H | 2,6-Cl(Ph) |
| 7.228 | $CF_3$ | $CH_3$ | 2,3,6-Cl(Ph) |
| 7.229 | $CF_3$ | $C_2H_5$ | 2,4,6-Cl(Ph) |
| 7.230 | $CF_3$ | $n-C_3H_7$ | 2,6-Cl(Ph) |
| 7.231 | $CF_3$ | $iso-C_3H_7$ | 2,3,6-Cl(Ph) |

Table 8: Compounds 8.1 to 8.231 are compounds of Formula I wherein A, $R_3$, $R_4$, and $R_5$ are hydrogen; X is N and Z is O; $R_1$ is methyl; and $R_2$, $R_6$, and $R_7$ are defined as in Table 7. Compounds 8.1 (oil, 9:1 A:B isomers), 8.1A (oil), 8.1B (oil); 8.7 (oil, 7.9:2.1 A:B isomers).

Table 9: Compounds 9.1 to 9.231 are compounds of Formula I wherein A, $R_3$, $R_4$, and $R_5$ are hydrogen; X is N and Z is NH, $R_1$ is methyl; and $R_2$, $R_6$, and $R_7$ are defined as in Table 7. Compounds 9.1 (oil, 9:1 A:B isomers), 9.1A (oil), 9.1B mpt 140–146° C.; 9.7A (oil) and 9.7B (oil).

Typical compounds of Formula I encompassed by the present invention wherein A, $R_3$, $R_4$, and $R_5$ are hydrogen; X is CH and Z is O; and $R_1$ is methyl include those compounds presented in Table 10 of Formula III where $R_2$, $R_6$, and $R_7$ are defined in Table 10.

Formula III

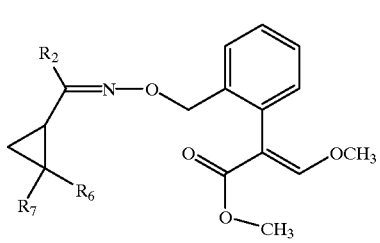

TABLE 10

| Compd # | $R_2$ | $R_6$ | $R_7$ |
|---|---|---|---|
| 10.1 | H | H | 2,4-Cl-pyrid-3-yl |
| 10.2 | H | H | 2,4-F-pyrid-3-yl |
| 10.3 | H | H | 2-Cl-4-F-pyrid-3-yl |
| 10.4 | H | H | 2,4-$(CH_3)_2$-pyrid-3-yl |
| 10.5 | H | H | 3,5-Cl-pyrid-4-yl |
| 10.6 | H | H | 3,5-F-pyrid-4-yl |
| 10.7 | H | H | 3-Cl-5-F-pyrid-4-yl |
| 10.8 | H | H | 3,5-$(CH_3)_2$-pyrid-4-yl |
| 10.9 | H | H | 4,6-Cl-pyrimidin-5-yl |
| 10.10 | H | H | 4,6-F-pyrimidin-5-yl |
| 10.11 | H | H | 4,6-$(CH_3)_2$-pyrimidin-5-yl |
| 10.12 | H | H | 4-Cl-6-F-pyrimidin-5-yl |
| 10.13 | $CH_3$ | H | 2,4-Cl-pyrid-3-yl |
| 10.14 | $CH_3$ | H | 2,4-F-pyrid-3-yl |
| 10.15 | $CH_3$ | H | 2-Cl-4-F-pyrid-3-yl |
| 10.16 | $CH_3$ | H | 2,4-$(CH_3)_2$-pyrid-3-yl |
| 10.17 | $CH_3$ | H | 3,5-Cl-pyrid-4-yl |
| 10.18 | $CH_3$ | H | 3,5-F-pyrid-4-yl |
| 10.19 | $CH_3$ | H | 3-Cl-5-F-pyrid-4-yl |
| 10.20 | $CH_3$ | H | 3,5-$(CH_3)_2$-pyrid-4-yl |
| 10.21 | $CH_3$ | H | 4,6-Cl-pyrimidin-5-yl |
| 10.22 | $CH_3$ | H | 4,6-F-pyrimidin-5-yl |
| 10.23 | $CH_3$ | H | 4,6-$(CH_3)_2$-pyrimidin-5-yl |
| 10.24 | $CH_3$ | H | 4-Cl-6-F-pyrimidin-5-yl |

TABLE 10-continued

| Compd # | $R_2$ | $R_6$ | $R_7$ |
|---|---|---|---|
| 10.25 | $CH_3$ | H | 3,5-Cl-pyridazin-4-yl |
| 10.26 | $CH_3$ | H | 3,5-F-pyridazin-4-yl |
| 10.27 | $CH_3$ | H | 3,5-Br-pyridazin-4-yl |
| 10.28 | $CH_3$ | H | 3,5-$(CH_3)_2$-pyridazin-4-yl |
| 10.29 | $CH_3$ | H | 3-Cl-5-F-pyridazin-4-yl |
| 10.30 | $CH_3$ | H | 5-Cl-3-F-pyridazin-4-yl |
| 10.31 | $CH_3$ | H | 3-Br-5-Cl-pyridazin-4-yl |
| 10.32 | $CH_3$ | H | 5-Br-3-Cl-pyridazin-4-yl |
| 10.33 | $CH_3$ | H | 2,4-Cl-thien-3-yl |
| 10.34 | $CH_3$ | H | 2,4-F-thien-3-yl |
| 10.35 | $CH_3$ | $CH_3$ | 2-Cl-4-F-thien-3-yl |
| 10.36 | $CH_3$ | $CH_3$ | 2-F-4-Cl-thien-3-yl |
| 10.37 | $CH_3$ | $CH_3$ | 2,4-$(CH_3)_2$-thien-3-yl |
| 10.38 | $CH_3$ | $CH_3$ | 2,4,5-Cl-thien-3-yl |
| 10.39 | $CH_3$ | $CH_3$ | 2,4,5-F-thien-3-yl |
| 10.40 | $CH_3$ | $CH_3$ | 2,4,5-$CH_3$-thien-3-yl |
| 10.41 | $CH_3$ | $CH_3$ | 2,4-Cl-furan-3-yl |
| 10.42 | $CH_3$ | $CH_3$ | 2,4-F-furan-3-yl |
| 10.43 | $CH_3$ | $CH_3$ | 2-Cl-4F-furan-3-yl |
| 10.44 | $CH_3$ | $CH_3$ | 2-F-4Cl-furan 3-yl |
| 10.45 | $CH_3$ | $CH_3$ | 2,4-$(CH_3)_2$-furan-3-yl |
| 10.46 | $CH_3$ | $CH_3$ | 2,4,5-Cl-furan-3-yl |
| 10.47 | $CH_3$ | $CH_3$ | 2,4,5-F-furan-3-yl |
| 10.48 | $CH_3$ | $CH_3$ | 2,4,5-$CH_3$-furan-3-yl |
| 10.49 | $CH_3$ | $CH_3$ | 2,4-Cl-1-$CH_3$-1H-pyrrol-3-yl |
| 10.50 | $CH_3$ | $CH_3$ | 2,4-F-1-$CH_3$-1H-pyrrol-3-yl |
| 10.51 | $CH_3$ | $CH_3$ | 2-Cl-4F-1-$CH_3$-1H-pyrrol-3-yl |
| 10.52 | $CH_3$ | $CH_3$ | 2-F-4Cl-1-$CH_3$-1H-pyrrol-3-yl |
| 10.53 | $CH_3$ | $CH_3$ | 3,5-Cl-isoxazol-4-yl |
| 10.54 | $CH_3$ | $CH_3$ | 3,5-F-isoxazol-4-yl |
| 10.55 | $CH_3$ | $CH_3$ | 3,5-Br-isoxazol-4-yl |
| 10.56 | $CH_3$ | $CH_3$ | 3,5-$CH_3$-isoxazol-4-yl |
| 10.57 | $CH_3$ | $CH_3$ | 3,5-$CH_3O$-isoxazol-4-yl |
| 10.58 | $CH_3$ | $CH_3$ | 3,5-$CF_3O$-isoxazol-4-yl |
| 10.59 | $CH_3$ | $CH_3$ | 3,5-Cl-isothiazol-4-yl |
| 10.60 | $CH_3$ | $CH_3$ | 3,5-F-isothiazol-4-yl |
| 10.61 | $CH_3$ | $CH_3$ | 3,5-Br-isothiazol-4-yl |
| 10.62 | $CH_3$ | $CH_3$ | 3,5-$CH_3$-isothiazol-4-yl |
| 10.63 | $CH_3$ | $CH_3$ | 3,5-$CH_3O$-isothiazol-4-yl |
| 10.64 | $CH_3$ | $CH_3$ | 3,5-$CF_3O$-isothiazol-4-yl |
| 10.66 | $CH_3$ | $CH_3$ | 3,5-Cl-1-$CH_3$-1H-pyrazol-4-yl |
| 10.67 | $CH_3$ | $CH_3$ | 3,5-F-1-$CH_3$-1H-pyrazol-4-yl |
| 10.68 | $CH_3$ | $CH_3$ | 3,5-Br-1-$CH_3$-1H-pyrazol-4-yl |
| 10.69 | $CH_3$ | $CH_3$ | 3-Cl-SF-1-$CH_3$-1H-pyrazl-4-yl |
| 10.70 | $CH_3$ | $CH_3$ | 2,4-Cl-pyrid-3-yl |
| 10.71 | $CH_3$ | $C_2H_5$ | 2,4-F-pyrid-3-yl |
| 10.72 | $CH_3$ | $n-C_3H_7$ | 2-Cl-4-F-pyrid-3-yl |
| 10.73 | $CH_3$ | $iso-C_3H_7$ | 2,4-$(CH_3)_2$-pyrid-3-yl |
| 10.74 | $CH_3$ | $n-C_4H_9$ | 3,5-Cl-pyrid-4-yl |
| 10.75 | $CH_3$ | $iso-C_4H_9$ | 3,5-F-pyrid-4-yl |
| 10.76 | $CH_3$ | $CH_2=CH$ | 3-Cl-5-F-pyrid-4-yl |
| 10.77 | CN | $CH_3CH=CH$ | 2,4-Cl-pyrid-3-yl |
| 10.78 | CN | $CH_3$ | 2,4-F-pyrid-3-yl |
| 10.79 | CN | $CH_3$ | 2-Cl-4-F-pyrid-3-yl |
| 10.80 | CN | $CH_3$ | 2,4-$(CH_3)_2$-pyrid-3-yl |
| 10.81 | CN | $CH_3$ | 3,5-Cl-pyrid-4-yl |
| 10.82 | CN | $CH_3$ | 3,5-F-pyrid-4-yl |
| 10.83 | CN | $CH_3$ | 3-Cl-5-F-pyrid-4-yl |
| 10.84 | CN | $CH_3$ | 4,6-Cl-pyrimidin-5-yl |
| 10.85 | CN | $CH_3$ | 4,6-F-pyrimidin-5-yl |
| 10.86 | CN | $CH_3$ | 2,4-Cl-thien-3-yl |
| 10.87 | CN | $CH_3$ | 2,4-F-thien-3-yl |
| 10.88 | CN | $CH_3$ | 2-Cl-4-F-thien-3-yl |
| 10.89 | CN | $CH_3$ | 2-F-4-Cl-thien-3-yl |
| 10.90 | CN | $CH_3$ | 2,4-$(CH_3)_2$-thien-3-yl |
| 10.89 | CN | $CH_3$ | 2,4,5-Cl-thien-3-yl |
| 10.90 | CN | $CH_3$ | 2,4,5-F-thien-3-yl |
| 10.91 | CN | $CH_3$ | 2,4,5-$CH_3$-thien-3-yl |
| 10.92 | CN | $C_2H_5$ | 2,4-Cl-pyrid-3-yl |
| 10.93 | CN | $n-C_3H_7$ | 2,4-Cl-pyrid-3-yl |
| 10.94 | CN | $iso-C_3H_7$ | 2,4-Cl-thien-3-yl |
| 10.95 | CN | $n-C_4H_9$ | 2,4-F-thien-3-yl |
| 10.96 | CN | $iso-C_4H_9$ | 2-Cl-4-F-thien-3-yl |
| 10.97 | CN | $CH_2=CH$ | 2-F-4-Cl-thien-3-yl |
| 10.98 | CN | $CH_3CH=CH$ | 2,4-$(CH_3)_2$-thien-3-yl |
| 10.99 | $CF_3$ | $CH_3$ | 2,4-Cl-pyrid-3-yl |

TABLE 10-continued

| Compd # | R$_2$ | R$_6$ | R$_7$ |
|---|---|---|---|
| 10.100 | CF$_3$ | CH$_3$ | 2,4-F-pyrid-3-yl |
| 10.101 | CF$_3$ | CH$_3$ | 2,4-Cl-thien-3-yl |
| 10.102 | CF$_3$ | CH$_3$ | 2,4-F-thien-3-yl |
| 10.103 | CF$_3$ | CH$_3$ | 2-Cl-4-F-thien-3-yl |
| 10.104 | CF$_3$ | CH$_3$ | 2-F-4-Cl-thien-3-yl |
| 10.105 | CH$_3$ | CH$_3$ | 2,4-(CH$_3$)$_2$-thien-3-yl |
| 10.106 | CH$_3$ | CH$_3$ | 3,5-Cl-isothiazol-4-yl |
| 10.107 | CH$_3$ | CH$_3$ | 3,5-F-isothiazol-4-yl |
| 10.108 | CH$_3$ | n-C$_3$H$_7$ | 2,4-Cl-pyrid-3-yl |
| 10.109 | CH$_3$ | iso-C$_3$H$_7$ | 2,4-F-pyrid-3-yl |
| 10.110 | CH$_3$ | n-C$_4$H$_9$ | 3,5-Cl-pyrid-4-yl |
| 10.111 | CH$_3$ | iso-C$_4$H$_9$ | 3,5-F-pyrid-4-yl |
| 10.112 | CH$_3$ | CH$_2$=CH | 2,4-Cl-pyrid-3-yl |
| 10.113 | CH$_3$ | CH$_3$CH=CH | 2,4-F-pyrid-3-yl |

Table 11: Compounds 11.1 to 11.113 are compounds of Formula I wherein A, R$_3$, R$_4$, and R$_5$ are hydrogen; X is N and Z is O; R$_1$ is methyl; and R$_2$, R$_6$, and R$_7$ are defined as in Table 7.

Table 12: Compounds 12.1 to 12.113 are compounds of Formula I wherein A, R$_3$, R$_4$, and R$_5$ are hydrogen; X is N and Z is NH, R$_1$ is methyl; and R$_2$, R$_6$, and R$_7$ are defined as in Table 7.

As used in Tables 1 to 12 Ph is understood to be phenyl.

Compounds of the present invention are prepared according to the following synthetic schemes. Scheme A describes the preparation of compounds of the Formula (I) where A and R$_2$ to R$_7$ are as defined in Tables 1–2, 4–5, 7–8, and 10–11; X is CH or N, and Z is O (compounds of Formula VI and VII). The cyclopropyl oximes (V) are reacted with the appropriately substituted benzyl derivatives (IV), where Z is a halogen, such as bromo, chloro or iodo, preferably a benzyl bromide. A cyclopropyl substituted oxime represented by the general formula (V) is treated, at room temperature, with an appropriate base to form an anion, followed by the addition of the benzyl bromide (IV). Typical bases employed are metal hydrides such as sodium hydride, alkoxides such as sodium methoxide and hydroxide bases such as sodium or potassium hydroxide and alkali bases such as sodium or potassium carbonate. Typical solvents employed with hydride bases are N,N-dimethylformamide (DMF) and tetrahydrofuran (THF); with hydroxide bases DMF, THF, methyl ethyl ketone (MEK) and acetone and with alkali bases solvents such as DMF, acetone, and MEK.

As shown in Scheme A, the N—O bond in C(R$_2$)=N—O—, appears in the E position (assuming

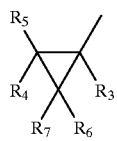

is the larger substituent). It should be recognized that the Z isomer can also be produced as well as mixtures. When isomers are produced they are designated isomer A (higher R$_f$ on thin layer chromatography) and isomer B (lower R$_f$ on thin layer chromatography). The determination of which isomer, A or B possesses the E or Z geometry can be made by such conventional techniques as X ray crystallography or by spectroscopic means such as nuclear magnetic resonance spectroscopy. For the compounds of the present invention isomer A has been assigned the E iminoxy configuration and isomer B, the Z iminoxy configuration.

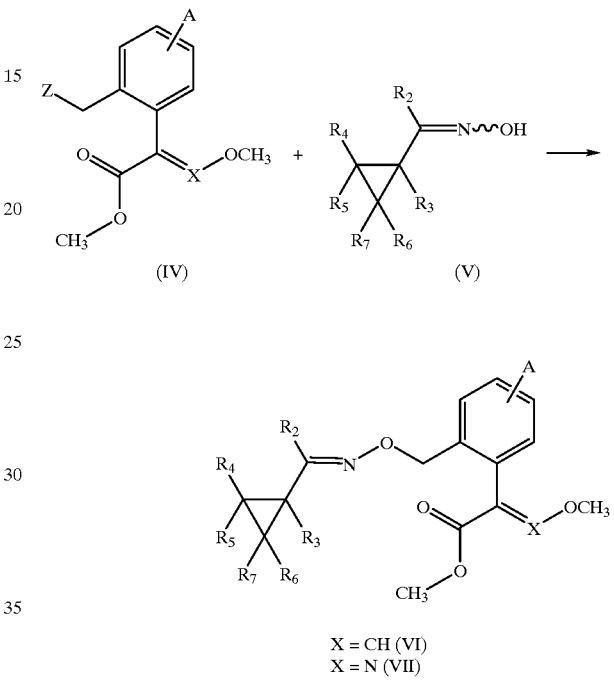

Scheme A

Compounds of formula VI (X is CH) are prepared by alkylation with methyl E-α-(2-bromomethylphenyl)-β-methoxyacrylate in the presence of a base, preferably NaOH or KOH, in a solvent, preferably acetone or methyl ethyl ketone. Methyl E-α-(2-bromomethylphenyl)-β-methoxyacrylate, as a single E isomer, can be prepared in two steps from 2-methylphenylacetate as described previously in U.S. Pat. No. 4,914,128, columns 3–4. Compounds of formula VII (X=N) are prepared by the reaction with methyl E-2-(bromomethyl)phenylglyoxylate O-methyloxime in the presence of a base, preferably NaOH or KOH, in a solvent, preferably acetone or methyl ethyl ketone. Methyl 2-(bromomethyl)phenylglyoxylate O-methyloxime can be prepared as described in U.S. Pat. No. 4,999,042, columns 17–18 and U.S. Pat. No. 5,157,144, columns 17–18. Methyl 2-(bromomethyl)phenylglyoxylate O-methyloxime is prepared from methyl 2-methylphenyl-acetate by treatment with an alkyl nitrite under basic conditions to provide after methylation, methyl 2-methyl-phenyl-glyoxalate O-methyl oxime which can also be prepared from methyl 2-methyl-phenylglyoxalate by treatment with 2-hydroxylamine hydrochloride and methylation or by treatment with methoxylamine hydrochloride.

Scheme B

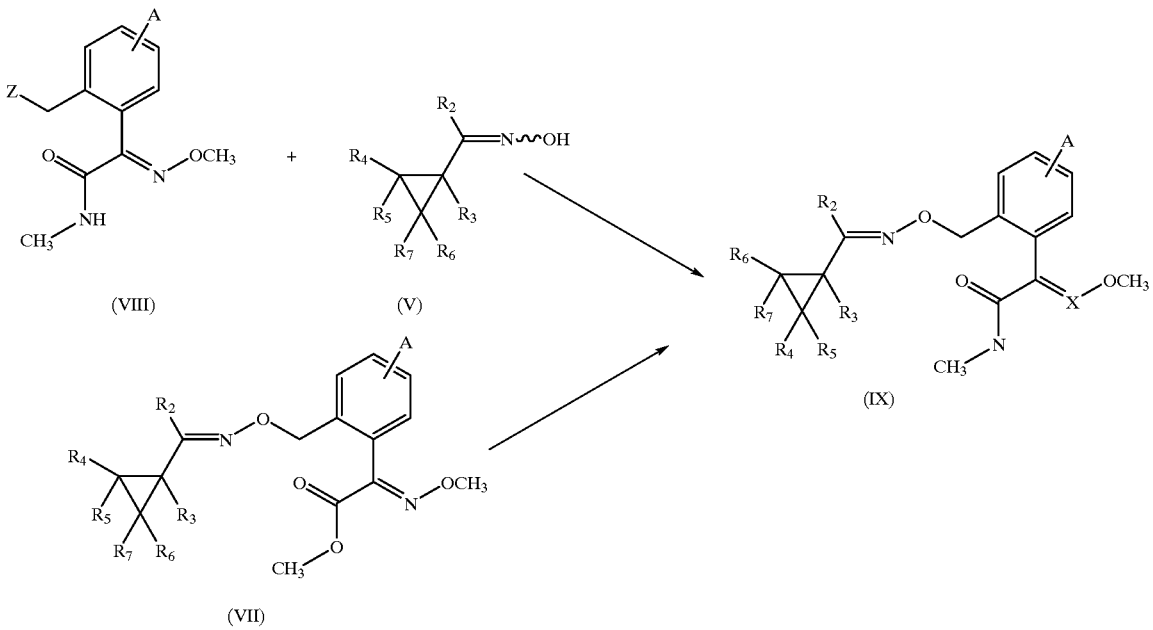

As shown in scheme B compounds of formula IX (X is N) and of Tables 3, 6, 9, and 12 can be prepared by the aminolysis of oximinoacetate (VII). The aminolysis of oximinoacetate to oximinoacetamides has been described in U.S. Pat. No. 5,185,342, cols. 22, 48 and 57, U.S. Pat. No. 5,221,691, cols. 26–27 and U.S. Pat. No. 5,407,902, col. 8. For example, compounds of formula VII and of Table 2 are treated with 40% aqueous methylamine in methanol to provide compounds of formula IX and of Table 3 of formula I where Z is NH. Alternatively, as is shown in scheme B intermediate unsaturated oximes (V) are reacted with N-methyl (E)-2-methoxyimino-2-[2-(bromomethyl)phenyl] acetamide VIII in the presence of a base such as an hydroxide base preferably in a solvent such as acetone or methyl ethyl ketone to provide compounds of formula (IX). N-methyl (E)-2-methoxy-imino-2-[2-(bromomethyl) phenyl]acetamide is described in U.S. Pat. No. 5,387,714, col. 13.

The oximes of the general formula (V) can be obtained, as shown in Scheme C, by reacting the corresponding cyclopropyl aldehyde or ketone (X) with hydroxylamine hydrochloride from room temperature to reflux, preferably at room temperature, in an appropriate solvent such as methanol or ethanol in the presence of an appropriate alkali such as sodium hydroxide, potassium carbonate or pyridine. A general description of the synthesis of oximes with hydroxylamine is described in March, *Advanced Organic Chemistry*, 4th Ed, pp. 906–907 and references therein. The oximes of the general formula (III) when obtained as a mixture of syn or anti oxime isomers can be separated into individual isomers and alkylated as described in scheme A and B. When a mixture of oximes of the general formula (III) are used in Schemes A and B the compounds of the formula VI, VII and IX can be separated into their individual isomers by conventional chromatographic techniques.

Scheme C

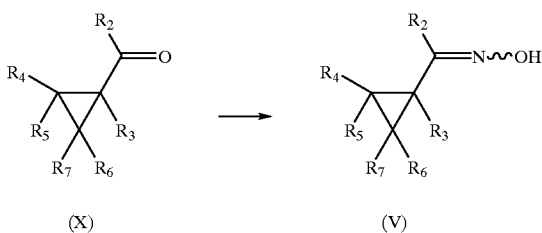

The cyclopropyl aldehydes or ketones (X) are prepared by conventional techniques. The unsaturated intermediate XI (Scheme D) is reacted with a sulfur ylide, prepared from a dimethylsulfoxonium salt in the presence of a base, resulting in the substituted acyl cyclopropanes, X, as shown in Scheme D. The chemistry of sulfur ylides is described in Trost and Melvin, *Sulfur Ylids,* Academic Press, New York, N.Y. 1975 and in Block, *Reactions of Organosulfur Compounds,* pp. 91–123, Academic Press, New York, N.Y. 1978. Typical reaction conditions for sulfur ylide formation from a dimethylsulfoxonium salt utilizes bases such as hydroxides, metal hydrides and alkoxides in solvents such as dimethoxyethane, dimethylsulfoxide and water depending on the base employed. The reactions are conducted from 0 to 20° C. preferably from 10–15° C. and preferably with alkali metal hydroxides in dimethylsulfoxide. Typically dimethylsulfoxonium methylide is prepared from trimethylsulfoxonium iodide in dimethylsulfoxide in the presence of powdered sodium hydroxide at room temperature. The unsaturated aldehydes or ketones (XI) are added dropwise to the ylide and stirred at room temperature.

Scheme D

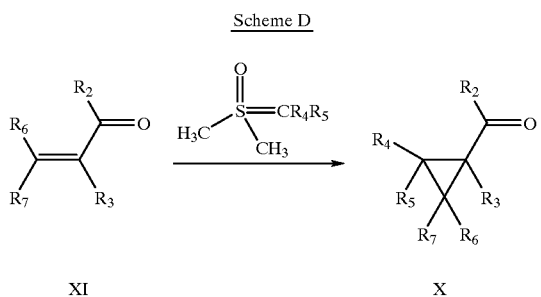

The α,β-unsaturated aldehydes or ketones XI can be prepared by conventional condensation techniques. A extensive description of the synthesis of α,β-unsaturated aldehydes or ketones (enones) is described in March, *Advanced Organic Chemistry*, 4th Ed, pp. 937–955 and references therein. For example *Organic Reactions*, Volume 16 describes the general aldol condensation of ketones and aldehydes. For intermediates of formula XI of this invention, in general the ketones and aldehydes are $R_7COR_6$ (XII) and $R_2COCH_2R_3$ (XIII) where $R_2$, $R_3$, $R_6$, and $R_7$ are defined previously. When $R_6$ is hydrogen, the aldehydes $R_7CHO$ (XIV), are for example benzaldehydes (arylCHO) or heterocyclic aldehydes substituted with from 2 to 5 substituents wherein the positions on the aryl and heterocyclic ring adjacent to the bond to the cyclopropyl ring, in Formula I, are both substituted. These substituted benzaldehyes or heterocyclic aldehydes are commerically available or prepared by conventional techniques. The aldehydes $R_7CHO$ (XIV) are reacted with the ketones $R_2COCH_2R_3$, XIII, (as shown in Scheme E) to provide the intermediates enones XV. Typically the ketone, $R_2COCH_2R_3$, is dissolved in a hydroxylic solvent, such as methanol or ethanol, to which is added dropwise the aldehyde $R_7CHO$ followed by the base or alternatively a solution of the aldehyde in an aqueous basic solution is added. The typical bases used can be alkali metal hydroxides, such as barium, potassium or sodium hydroxide and the dropwise addition is conducted from 0° C. to 35° C. preferably at ambient temperature. When the enone is derived from acetone ($R_2$ is methyl and $R_3$ is hydrogen) the solvent can be acetone to which is added $R_7COR_6$ followed by the aqueous hydroxide solution. Preferably the aldehyde is dissolved in a solvent mixture of acetone:water (1:5) to which is added the base while stirring at room temperature.

Scheme E

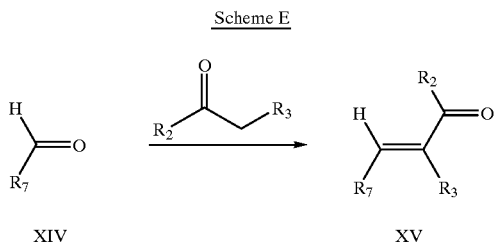

When $R_6$ is not hydrogen, $R_7COR_6$ (XII) are the ketones arylCOR$_6$ or heterocyclic ketones, substituted with from 2 to 5 substituents wherein the positions on the aryl and heterocyclic rings adjacent to the bond to the cyclopropyl ring, in Formula I, are both substituted or aryl or heterocyclic ring is unsubstituted or substituted from 1 to 4 substituents wherein at least one of the positions on the aryl or heterocyclic rings adjacent to the bond to the cyclopropyl ring, in Formula I, is a hydrogen. For the compounds of formula I where $R_6$ is not hydrogen the intermediate unsaturated aldehydes and ketones XI are prepared, as shown in Scheme F, according to the procedures described in U.S. Pat. No. 3,950,427, col. 17 line 20, to provide after purification the E diastereiosmer ($R_7$ is trans to $R_2CO$ in XI). In a typical preparation a ketone such as $R_7COR_6$ is reacted with an ethyl trans 3-ethoxycrotonate in dimethylformamide in the presence of potassium t-butoxide followed by acidic hydrolysis and decarboxylation to give XI. The crotonates, XVI, can be prepared from substituted ethyl acetoketones by conventional techniques

Scheme F

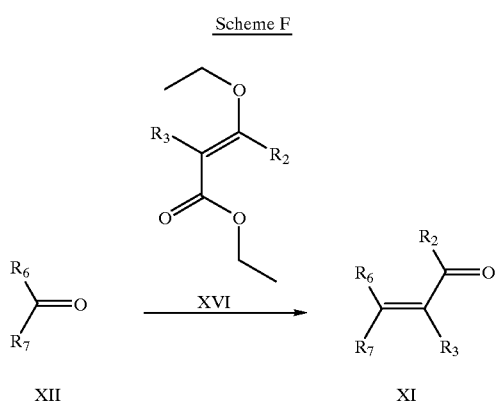

Alternatively the α,β-unsaturated cyclopropyl ketones X can be prepared from cyclopropyl nitriles XIV which are prepared via cyclopropanation of the acrylonitriles XVIII as is described in Scheme G. The acrylonitriles XVIII starting materials, shown in Scheme G can be prepared by conventional synthetic methods as described in March, Advanced Organic Chemistry, 4th Ed, pp. 937–955 and references therein. For example the nitrile derivative $R_3CH_2CN$ is condensed with the ketone or aldehyde $R_7COR_6$, in the presence of a base to provide the acrylonitriles XIII. Typically the a nitrile is dissolved in a solvent such as ethanol and water to which is added the aldehyde or ketone followed by a base. Typical bases used can be alkali metal hydroxides, such as barium, potassium or sodium hydroxide and the mixture is stirred typically at ambient temperature.

The acrylonitrile XVIII is treated as is described in Scheme D with a sulfur ylide to provide the cyclopropyl nitriles XVII. The cyclopropyl nitrile XVII is transformed to the cyclopropyl ketone by organometallic addition to the nitrile followed by hydrolysis. For example the standard Grignard reagents $R_2MgX$ or organolithium reagents, $R_2Li$, add to the nitrile functionality to provide the ketone X. The addition reaction to nitriles is described in March, Advanced Organic Chemistry, 4th Ed, pp.935–936 and references cited therein. The cyclopropyl nitrile XVII can be transformed to the cyclopropyl aldehyde X' (where $R_2$ is H) by standard reductive methods such as with diisobutylaluminum hydride (DiBAL). The formation of aldehydes from the reduction of nitrites is described in March, Advanced Organic Chemistry, 4th Ed, pp.919–920 and references cited therein.

Scheme G

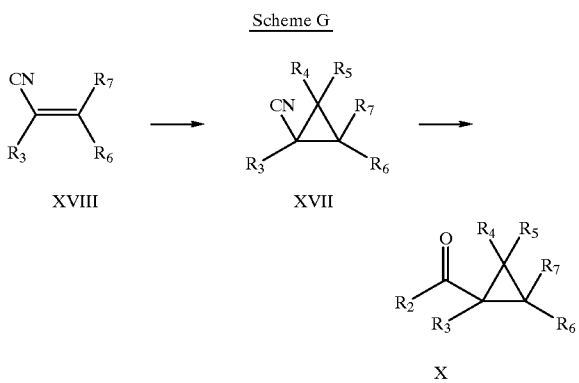

A direct synthesis of compounds of the formula VII or IX is shown in Scheme H. Compounds of the Formula VII or IX can be prepared directly from the functionalized cyclopropyl ketones or aldehydes, X, by condensation with the aminoxy intermediate XIX. The preparation of aminoxy intermediate XIX is described in U.S. Pat. No. 5,194,662. The aminoxy intermediate XIX is prepared in a two step sequence by the alkylation of IV (where X is N) with N-hydroxyphthalimide which is treated with hydrazine to provide XIX. The aminoxy intermediate XIX is condensed with ketones or aldehydes X to provide VII which are treated as shown in scheme B to provide IX.

Scheme H

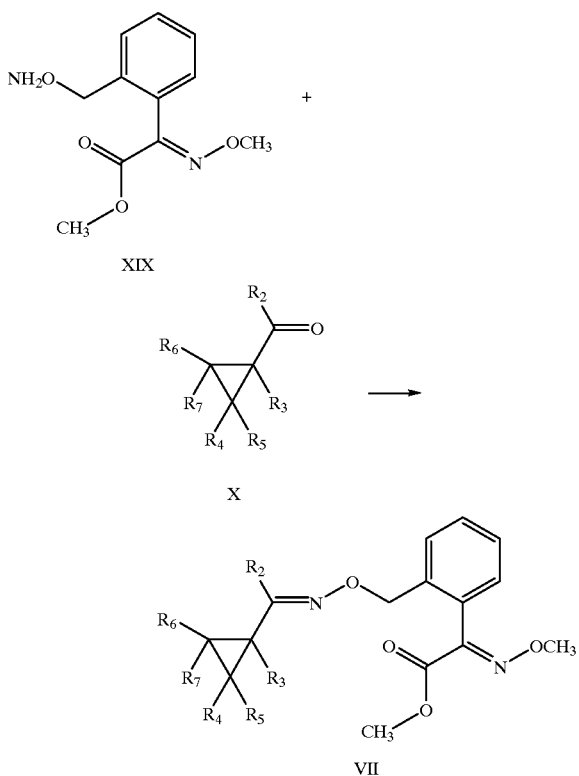

The compounds of this invention can be made according to the following procedures:

EXAMPLE 1

Preparation of E and Z imine isomers: (E,E) and (Z,E) Methyl 2-[2-((trans-1-(2-(2',6'-dichlorophenyl)cyclopropyl)ethylidene)aminooxymethyl)phenal]-2-methoxyiminoacetate Compound 8.1, 8.1A and 8.1B of Table 8

Preparation of 4-(2,6-dichlorophenyl)-3-buten-2-one

To a 1000 ml round bottom flask equipped with mechanical stirrer, and nitrogen inlet were charged 26.5 g (0.15 moles) of 4-chlorobenzaledhyde, 125 mls of acetone, 600 mls of water, and 9.3 g (0.23 moles) of sodium hydroxide. The mixture was stirred for 12 hours at room temperature. Analysis of an aliquot by GC indicated complete reaction. The resulting solid was collected by vacuum filtration, and washed with 100 mls of water, 100 mls of hexane, and dried in vacuuo at 40° C. for 3 hours. 31.4 g of the title compound, 4-(2,6-dichlorophenyl)-3-buten-2-one, was isolated as a pale yellow solid in 98% isolated yield.

NMR 300 MHz $^1$H CDCl$_3$ 2.43 (s, 3H); 6.80 (d, 1H); 7.18–7.38 (m, 1H); 7.4 (d, 2H); 7.6 (d, 1H).

Preparation of trans-1-(2,6 dichlorophenyl)-2-acetyl-cyclopropane

To a 1000 ml round bottom flask equipped with magnetic stirrer, nitrogen inlet and addition funnel were charged 33.2 g (0.151 moles) of trimethyl sulfoxonium iodide, 6.1 g (0.151 moles) of powdered sodium hydroxide, and 300 mls DMSO. The mixture was stirred at room temperature for 1 hour, followed by the rapid addition of the 4-(2,6-dichlorophenyl)-3-buten-2-one (32.3 g, 0.151 moles) in one portion. The reaction was then stirred for 10 minutes at ambient temperature, then poured into 200 mls of ice water and extracted with 3×100 ml of ethyl ether. The ether extract was washed with 2×100 mls of water, 100 mls of brine, dried over anhydrous MgSO$_4$, filtered through 2" of silica gel, and concentrated in vacuuo on a rotary evaporator to afford 31.7 g of a thick pale yellow oil which was chromatographed on silica gel with 90% hexane, 10% ethyl acetate. The pure fractions were combined and concentrated in vacuuo on a rotary evaporator to afford 27.9 g of trans-1-(2,6 dichlorophenyl)-2-acetyl-cyclopropane as a free flowing pale yellow liquid in 81% yield.

NMR 300 MHz $^1$H CDCl$_3$ 1.4–1.48 (m, 1H); 1.78–1.86 (m, 1H); 2.21–2.30 (m, 1H); 2.34–2.4 (m, 1H); 2.41 (s, 3H), 7.2 (m, 1H), 7.3 (d, 2H).

Preparation of E and Z imine isomers: (E,E) and (Z,E) Methyl 2-[2-((trans-1-(2-(2',6'-dichlorophenyl)cyclopropyl)ethylidene)aminooxymethyl)phenyl]-2-methoxyiminoacetate To a 100 ml round bottom flask equipped with magnetic stirrer were charged 1.0 g (0.0044 moles) of the trans-1-(2,6 dichlorophenyl)-2-acetyl-cyclopropane, 1.1 g (0.0044 moles) of the methyl (E)-2-(aminooxymethyl)phenyl glyoxylate O-methyloxime, and 50 mls of anhydrous methanol. The reaction was stirred overnight at room temperature. Analysis of an aliquot by GC indicated no starting material and two new products. The reaction was then poured into 100 mls of water and extracted with 3×50 ml of ethyl ether. The ether extract was washed with 100 mls of water, 100 mls of 0.1N HCl, and 100 mls of brine, dried over anhydrous magnesium sulfate, filtered, and concentrated in vacuuo on a rotary evaporator to afford 2.0 g of a thick yellow oil which was chromatographed on silica with 20% ethyl acetate/80% hexane. The pure fractions were combined and concentrated in vacuuo on a rotary evaporator to afford 1.4 g of the methyl 2-[2-((trans-1-(2-(2',6'-dichlorophenyl)cyclopropyl)ethylidene)aminooxymethyl)phenyl]-2-methoxyiminoacetate as a pale yellow oil as a 90/10 A:B (E,E:E,Z) isomer ratio in 72% isolated yield.

NMR 300 MHz $^1$H CDCl$_3$ 1.3 (m, 1H); 1.7 (m, 1H); 1.85 (s, 3H); 1.95 (m, 1H); 2.2 (m, 1H); 3.85 (s, 3H); 4.1 (s, 3H); 5.0 (s, 2H); 7.1 (m, 1H), 7.2 (m, 1H); 7.3 (d, 2H); 7.4–7.6 (m, 3H).

An additional 10.0 g of the crude product as an orange oil (85% chemically pure and 2:1 A:B isomers) was chromatographed on silica with 20% ethyl acetate/80% hexane.

5.02 grams of isomer A as a pale yellow oil was collected (E:E)-methyl 2-[2-((trans-1-(2-(2',6'-dichlorophenyl)cyclopropyl)ethylidene)aminooxymethyl)phenyl]-2-methoxyiminoacetate.

Compound 8.1A, Isomer A, E imine, NMR (300 MHz., $^1$H CDCl$_3$): 1.19–1.30 (1H, m), 1.50–1.58 (1H, m), 1.75–1.85 (1H, m) 1.84 (3H, s), 2.06–2.14 (1H, m), 3.85 (3H, s), 4.05 (3H, s), 4.98 (2H, s), 7.03–7.49 (7H, m).

0.825 grams of isomer B as a pale yellow oil was collected (Z:E)-methyl 2-[2-((trans-1-(2-(2',6'-dichlorophenyl)cyclopropyl)ethylidene)aminooxymethyl)phenyl]-2-methoxyiminoacetate.

Compound 8.1B, Isomer B, Z imine, NMR (300 MHz., $^1$H CDCl$_3$): 1.21–1.28 (1H, m), 1.40–1.52 (1H, m), 1.70 (3H, s), 2.18–2.23 (1H, m) 2.61–2.70 (1H, m), 3.80 (3H, s), 4.00 (3H, s), 4.97 (2H, s), 7.05–7.52 (7H, m).

Preparation of methyl (E)-2-(aminooxymethyl)phenyl glyoxylate O-methyloxime Methyl (E)-2-(O-phthalimidoxymethyl)phenyl glyoxylate O-methyloxime To a dry 500 ml round bottom flask equipped with magnetic stirrer, and nitrogen inlet were charged 5.1 g (0.0315 moles) of N-hydroxyphthalimide, 1.3 g (0.0315 moles) of sodium hydroxide, and 300 ml of anhydrous dimethylformamide. The dark red solution was stirred at ambient temperature for 20 min., followed by the addition of the methyl 2-(bromomethyl)phenylglyoxylate O-methyloxime (15 g, 60% pure, 0.0315 moles) in one portion. The reaction was stirred at ambient temperature over the weekend, then poured into 800 mls of water and stirred for 1 hour to afford a white solid which was collected by vacuum filtration and washed with water, hexane, and dried under vacuum at 40° C. overnight. Isolated 11.5 g of a white solid (98% isolated yield) which was consistent with the desired product, methyl (E)-2-(O-phthalimidoxymethyl)phenyl glyoxylate O-methyloxime, upon analysis by 300 MHz $^1$H NMR (300 MHz, $^1$H, CDCl$_3$, TMS=0 ppm) 3.8 (s, 3H), 3.95 (s, 3H), 5.0 (s, 2H), 7.1 (d, 1H), 7.5 (m, 2H), 7.7–7.9 (m, 5H).

Preparation of methyl (E)-2-(aminooxymethyl)phenyl glyoxylate O-methyloxime

To a 250 ml round-bottom flask equipped with magnetic stirrer were charged 11.4 g (0.031 moles)of methyl (E)-2-(O-phthalimidoxymethyl)phenyl glyoxylate O-methyloxime 100 mls of anhydrous methanol, and 1.9 g (0.034 moles) of hydrazine monohydrate. The flask was stoppered, and the reaction was stirred at ambient temperature for 2 hours. The resulting solid was removed by filtration and the filtrate was concentrated on the rotary evaporator. The residue was dissolved in 100 mls of ether, filtered, and stripped to afford 7.4 g of a thick yellow oil (100% isolated yield). which was consistent with the desired product methyl (E)-2-(aminooxymethyl)phenyl glyoxylate O-methyloxime upon analysis by 300 MHz $^1$H NMR. Stored at −20° C. until needed for future synthesis.

NMR (300 MHz, 1H, CDCl$_3$, TMS=0 ppm) 3.87 (s, 3H), 4.03 (s, 3H), 4.6 (s, 2H), 4.9–5.4 (bs, 2H), 7.2 (m, 1H), 7.4–7.5 (m, 3H).

EXAMPLE 2

Preparation of E and Z imine isomers: (E,E) and (Z,E)-N-Methyl 2-[2-((trans-1-(2-(2',6'-dichlorophenyl)cyclopropyl)ethylidene)aminooxymethyl)phenyl]-2-methoxyiminoacetamide Compounds 9.1, 9.1A, 9.1B of Table 9

To a 100 ml flask equipped with magnetic stirrer and were charged 0.7 g (0.00115 moles) of (E,E:Z,E)-methyl 2-[2-((trans-1-(2-(2',6'-dichlorophenyl)cyclopropyl)ethylidene)aminooxymethyl)phenyl]-2-methoxyiminoacetate, 50 mls of methanol, and 2 mls (0.026 moles) of 40% aqueous methyl amine solution. The mixture stirred at ambient temperature overnight, then poured into 200 mls of water and extracted with 3×100 ml of ethyl ether. The ether extract was washed with 2×100 mls of water, 100 mls of 0.1 N HCl, and 100 mls of brine, dried over anhydrous MgSO$_4$, filtered, and concentrated in vacuuo on a rotary evaporator to afford 0.6 g of N-Methyl 2-[2-((trans-1-(2-(2',6'-dichlorophenyl)cyclopropyl)ethylidene)aminooxymethyl)phenyl]-2-methoxyiminoacetamide as a thick viscous pale yellow oil. 90/10 A:B (E,E:Z,E) isomers ratio in 88% isolated yield.

NMR 300 MHz, $^1$H CDCl$_3$ 1.2 (m, 1H); 1.6 (m, 1H); 1.8 (s, 3H); 1.9 (m, 1H); 2.2 (m, 1H); 2.9 (d, 3H); 3.95 (s, 3H), 5.0 (s, 2H); 6.7 (bs, 1H); 7.1 (m, 1H), 7.2 (m, 1H); 7.3 (d, 2H); 7.4–7.6 (m, 3H).

Additionally each of 8.1A and 8.1B oxime esters was separately treated as above with methylamine.

Aminolysis of 5.01 grams of 8.1A (E,E isomer) gave 5.02 grams (100% yield) of (E,E)-N-methyl 2-[2-((trans-1-(2-(2',6'-dichlorophenyl)cyclopropyl)ethylidene)aminooxymethyl)phenyl]-2-methoxyiminoacetamide as an oil. The oil was treated with ether, concentrated and cooled in dry ice followed by the addition of hexane to complete the crystallization. The resulting crystals were filtered to give a solid mpt. 94–97° C. Compound 9.1A, Isomer A, E,E isomer, NMR (300 MHz, $^1$H CDCl$_3$): 1.20–1.30 (1H, m), 1.51–1.58 (1H, m), 1.80–1.89 (1H, m), 1.82 (3H, s), 2.2 (1H,m), 2.89 (3H, d), 3.96 (3H, s), 4.98 (2H, s), 6.70 (1H, br), 7.05–7.48 (7H, m).

Aminolysis of 0.825 grams of 8.1B (Z,E isomer) gave 0.825 grams (100% yield) of (Z,E)-N-methyl 2-[2-((trans-1-(2-(2',6'-dichlorophenyl)cyclopropyl)ethylidene)aminooxymethyl)phenyl]-2-methoxyiminoacetamide as solid, mpt. 140–146° C. Compound 9.1B, Isomer B, Z,E isomer, NMR (300 MHz, $^1$H CDCl$_3$):): 1.22–1.30 (1H, m), 1.40–1.51 (1H, m), 1.70 (3H, s), 2.15–2.23 (1H, m), 2.60–2.69 (1H,m), 2.85 (3H, d), 3.90 (3H, s), 4.97 (2H, s), 6.70 (1H, br), 7.09–7.51 (7H, m).

EXAMPLE 3

Preparation of E and Z imine isomers: (E,E) and (Z,E) Methyl 2-[2-((trans-1-(2-(2',6'-difluorophenyl)cyclopropylethylidene)aminooxymethylphenyl]-2-methoxyiminoacetate Compound 8.7 of Table 8

Preparation of 4-(2,6-difluorophenyl)-3-buten-2-one

To a 100 ml reaction bottle equipped with magnetic stir bar were charged 5.0 g (35.2 mmole) 2,6-difluorobenzaldehyde in 20 ml acetone, added 50% NaOH (42 mmole) in 60 ml water (exothermic) and stirred room temperature. The reaction was monitored by GLC and after 2 hours worked up. The reaction mixture was extracted with 50 ml CHCl$_3$, washed with 50 ml H$_2$O, dried over anhydrous MgSO$_4$, filtered, and removed solvent in vacuuo on a rotary evaporator to afford 5.7 g of 4-(2,6-difluoro-phenyl)-3-buten-2-one as a yellow oil (81% purity by GC) in 89.5% isolated yield.

NMR (300 MHz $^1$H CDCl$_3$): 2.4 (s, 3H); 6.9 (m, 3H); 7.3 (m, 1H); 7.6 (d, 1H).

Preparation of trans-1-(2,6 difluorophenyl)-2-acetyl-cyclopropane

To a 500 ml round bottom flask equipped with magnetic stirrer, nitrogen inlet and addition funnel was charged 2.47 g (11.2 mmoles) of trimethyl sulfoxonium iodide, 0.448 g (11.2 mmole) of powdered sodium hydroxide, and 50 mls DMSO. The mixture was stirred at room temperature for 0.5 hour, followed by the rapid addition of 2.04 g (11.2 mmole) 2,6-difluoro-phenyl-3-buten-2-one in 25 ml DMSO in one portion. The reaction was stirred for 15 minutes at ambient temperature, poured into 200 mls of ice water, and then extracted with 150 ml of ethyl ether. The ether extract was washed with 4×100 mls of water, dried over anhydrous $MgSO_4$, filtered, and concentrated in vacuuo on a rotary evaporator to afford 1.3 g crude product as a yellow oil. This was combined with 1.6 g from a similar reaction and the total crude of 2.9 g was chromatographed on silica with $CH_2Cl_2$. Fractions (#5–9) were combined and concentrated in vacuuo on a rotary evaporator to afford 1.5 g (92% purity by GC) of trans-1-(2,6 difluorophenyl)-2-acetylcyclopropane as a free flowing pale yellow liquid, in 28.8% yield.

NMR (300 MHz $^1$H CDCl3): 1.6 (m, 2H); 2.3 (s, 3H); 2.4 (m, 2H); 6.8 (m, 2H), 7.1 (m, 1H).

Preparation of E and Z imine isomers: (E,E) and (Z,E) Methyl 2-[2-((trans-1-(2-(2',6'-difluorophenyl)cyclopropyl) ethylidene)aminooxymethyl)phenyl]-2-methoxyiminoacetate To a 25 ml reaction vial equipped with magnetic stirrer were charged 1.0 g (0.0051 moles) of the trans-1-(2,6 difluorophenyl)-2-acetyl-cyclopropane and 1.33 g (0.0056 moles) of the methyl (E)-2-(aminooxymethyl)phenyl glyoxylate O-methyloxime in 5 mls of anhydrous methanol and 5 drops glacial acetic acid. The reaction was stirred 4 hours at room temperature with formation of precipitate. The sample was refrigerated overnight and then worked up. The white precipitate was filtered in vacuuo, washed with 2×10 ml hexane, and dried in the vacuum oven at ambient to afford 1.1 g of the methyl 2-[2-((trans-1-(2-(2',6'-difluorophenyl)cyclopropyl)ethylidene)aminooxymethyl) phenyl]-2-methoxyiminoacetate as a white solid, mpt. 81–88° C., as a 79:21 A:B (E:E,Z:E) isomer ratio in 51.9% isolated yield.

NMR (300 MHz $^1$H CDCl3): 1.4 (t, 2H); 1.65–1.8 (d, 3H); 2.1 (m, 2H); 3.8 (d, 3H), 4.0 (d, 3H); 5.0 (s, 2H); 6.8 (m, 2H), 7–7.2 (m, 2H); 7.3–7.5 (m, 3H).

EXAMPLE 4

Preparation of E and Z imine isomers: (E,E) and (Z,E)-N-Methyl 2-[2-((trans-1-(2-(2',6'-difluorophenyl)cyclopropyl)ethylidene) aminooxymethyl)phenyl]-2-methoxyiminoacetamide Compounds 9.7A, 9.7B of Table 9

To a 25 ml reaction test tube under nitrogen atmosphere were charged 0.95 g of (E,E:Z,E)-methyl 2-[2-((trans-1-(2-(2',6'-difluorophenyl)cyclopropyl)ethylidene) aminooxymethyl)phenyl]-2-methoxyiminoacetate (2.3 mmole) in 7 ml MeOH and 1.8 g 40% aqueous methyl amine (23 mmole) which was heated at 55–60 C. The reaction was monitored by TLC and worked up after 1.5 hours. Removed the methanol in vacuuo on the rotary evaporator at 30° C. To the residue was added 125 ml ethyl acetate and 50 ml water, partitioned, further washed the organic phase with 2×50 ml water, dried over anhydrous $MgSO_4$, filtered, and concentrated in vacuuo on the rotary evaporator at 40° C. to give 1 g of (E,E:Z,E)-N-methyl 2-[2-((trans-1-(2-(2',6'-difluorophenyl)cyclopropyl)ethylidene)aminooxymethyl) phenyl]-2-methoxyiminoacetamide as a 76:24 A:B (E,E:Z, E) isomer ratio. This mixture was chromatographed on silica with 1:2 ethyl acetate:hexane to afford both (E,E) and (Z,E) isomers of the N-methyl 2-[2-((trans-1-(2-(2', 6'difluorophenyl)cyclopropyl)ethylidene)aminooxymethyl) phenyl]-2-methoxyiminoacetamide. 700 mg of isomer-A (E,E) was isolated as a clear oil and 150mg isomer B (Z,E) was isolated also as a pale yellow oil. The chromatographed combined isolated yield was 89.5%.

Compound 9.7A, Isomer A, E,E isomer: NMR (300 MHz $^1$H CDCl3) 1.4 (t, 2H); 1.8 (s, 3H); 2.1 (m, 2H); 2.9 (d, 3H); 3.9 (s, 3H); 4.9 (s, 2H); 6.7 (bs, 1H); 6.8 (t, 2H); 7–7.2 (m, 2H); 7.3–7.5 (m, 3H).

Compound 9.7B, Isomer B, Z,E isomer NMR (300 MHz $^1$H CDCl3) 1.3 (m, 1H); 1.6 (m, 4H); 2.1 (m, 1H); 2.8 (m, 4H); 3.9 (s, 3H); 4.9 (s, 2H); 6.7 (bs, 1H); 6.8 (t, 2H); 7–7.2 (m, 2H); 7.3–7.5 (m, 3H).

EXAMPLE 5

Preparation of Methyl 2-[2-((1-(2-(4'-chlorophenol)-2-methylcyclopropyl)ethylidene)aminooxymethyl) phenyl]-2-methoxyiminoacetate Compound 2.14A of Table 2

Preparation of E and Z enone isomers of 4-(4-chlorophenyl)-3-penten-2-one

To a 500 ml round bottom flask equipped with magnetic stirrer, nitrogen inlet and addition funnel were charged 10 g (0.065 moles) of 4'-chloroacetophenone, 10.2 g (0.065 moles) of ethyl-trans-3-ethoxycrotonate, and 150 mls of dry dimethylformamide. To this solution was then added 7.3 g (0.065 moles) of potassium t-butoxide in one portion. The reaction was stirred at ambient temperature under nitrogen for a total of three days. The reaction mixture was then poured into 200 mls of water and the aqueous was extracted with 3×50 mls of ethyl ether to remove any unreacted starting material. The aqueous fraction was acidified to pH 2 with 1 N aqueous HCl, and extracted with 3×100 mls of ethyl ether. The ether extract was washed with 2×100 mls of water and 100 mls of saturated sodium chloride solution, dried over anhydrous magnesium sulfate, filtered, and concentrated on a rotary evaporator to afford 12.4 g of a tan solid. This solid was then stirred in 50 mls of conc. HCl for 2 hours at ambient temperature, then poured into 100 g of crushed ice, and extracted with 3×100 ml of ethyl ether. The ether extract was washed with 2×100 mls of water, 100 mls of brine, dried over anhydrous magnesium sulfate, filtered, and concentrated on a rotary evaporator to afford 7.6 g of a yellow liquid, 4-(4-chlorophenyl)-3-penten-2-one, which appeared to be a mixture of the E and Z enones, with some minor chemical impurities, in 59.3% crude yield. The product was used in the next step without further purification.

300 MHz $^1$H NMR (tms=0 ppm) 2.3 (s, 3H); 2.5 (s, 3H); 6.5 (s, 1H); 7.3–7.5 (m, 4H).

Preparation of trans and cis-1-(4-chlorophenyl)-1-methyl-2-acetylcyclopropane

To a 250 ml round bottom flask equipped with magnetic stirrer, nitrogen inlet and addition funnel were charged the trimethyl sulfoxonium iodide (8.5 g, 0.0386 moles), powdered sodium hydroxide (1.6 g, 0.0386 moles) and 100 mls of dry DMSO. The mixture was stirred at room temperature for 1 hour, followed by the rapid addition of the (E>Z)-4-(4-chlorophenyl)-3-penten-2-one (7.5 g, 0.0386 moles)) in 10 mls DMSO. The reaction was stirred for 3 days at ambient temperature, then poured into 200 mls of ice water and extracted with 3×100 ml of ethyl ether. The ether extract was washed with 2×100 mls of water, 100 mls of brine, dried over anhydrous $MgSO_4$, filtered through 2" of silica gel, and concentrated on a rotary evaporator to afford 3.2 g of a thick pale yellow oil which was chromatographed on silica gel with 10% ethyl acetate, 90% hexane. The pure fractions were combined and concentrated on the rotary evaporator to afford 1.4 g (17.2% isolated yield) of a pale yellow liquid which was consistent with trans and cis-1-(4-chlorophenyl)-1-methyl-2-acetylcyclopropane upon analysis by 300 Mz 1H NMR.

300 MHz $^1$H NMR (tms=0 ppm) 1.2 (m, 1H); 1.4 (s, 3H); 1.6 (m, 1H); 2.2 (m, 1H); 2.35 (s, 3H); 7.1–7.4 (m, 4H).

Preparation of Methyl 2-[2-((1-(2-(4'-chlorophenyl)-2-methylcyclopropyl)ethylidene)aminooxymethyl)phenyl]-2-methoxyiminoacetate To a 20 ml glass vial equipped with magnetic stirrer were charged the 1.0 g (0.0048 moles) of the trans and cis-1-(4-chlorophenyl)-1-methyl-2-acetylcyclopropane, 1.2 g (0.0048 moles) of the methyl (E)-2-(aminooxymethyl)phenyl glyoxylate O-methyloxime, and 10 mls of dry methanol. The vial was capped, and stirred overnight at ambient temperature. The reaction mixture was then poured into 100 mls of water and extracted with 3×100 ml of ethyl ether. The ether extract was washed with 2× 100 mls of water, 100 mls of 1 N HCl, and 100 mls of saturated sodium chloride solution, dried over anhydrous MgSO$_4$, filtered, and concentrated on a rotary evaporator to afford 1.6 g of a thick orange oil which was chromatographed on silica gel with 20% ethyl acetate, 80% hexane. The pure fractions after chromatography were combined and concentrated on a rotary evaporator to afford 0.75 g of a clear colorless viscous oil (36.5% isolated yield) which was consistent with isomer A, (E,E)-methyl 2-[2-((1-(2-(4'-chlorophenyl)-2-methylcyclopropyl)ethylidene)aminooxymethyl)phenyl]-2-methoxyiminoacetate upon analysis by 300 MHz $^1$H NMR with a 70:30 ratio of cyclopropane isomers.

300 MHz $^1$H NMR (tms=0 ppm) 1.15 (s, 3H) 1.2 (m, 1H); 1.4 (m, 1H); 1.6 (m, 1H); 2.0(s, 3H); 3.85 (s, 3H); 4.0 (s, 3H); 5.0 (s, 2H); 7.1–7.3 (m, 5H); 7.35–7.6 (m, 3H)

EXAMPLE 6

Preparation of (E,E)-N-Methyl 2-[2-((1-(2-(4'-chlorophenyl)-2-methyl cyclopropyl)ethylidene)aminooxymethyl)phenyl]-2-methoxyiminoacetamide Compound 3.14A of Table 3

To a 100 ml round bottom flask equipped with magnetic stirrer were charged 0.7 g (0.00163 moles) of the (E,E)-methyl 2-[2-((1-(2-(4'-dichlorophenyl)-2-methylcyclopropyl)ethylidene)aminooxymethyl)phenyl]-2-methoxyiminoacetate, 25 mls of anhydrous methanol, and 1 ml (0.0129 moles) of 40% methyl amine in water. The flask was stoppered, and stirred overnight at ambient temperature. The reaction mixture was then poured into 100 mls of water and extracted with 3×50 ml of ethyl ether. The ether extract was washed with 2×50 mls of water, 50 mls of 1 N HCl, 50 mls of saturated sodium chloride solution, dried over anhydrous MgSO$_4$, filtered, and concentrated on a rotary evaporator to afford 0.7 g of a yellow viscous oil which was chromatographed on silica gel with 20% ethyl acetate, 80% hexane. The pure fractions were combined and concentrated on a rotary evaporator to afford 0.55 g of a clear colorless viscous oil (79% isolated yield) which was consistent with isomer A (E,E)-N-methyl 2-[2-((1-(2-(4'-chlorophenyl)-2-methylcyclopropyl)ethylidene)aminooxymethyl)phenyl]-2-methoxyiminoacetamide upon analysis by 300 Mz $^1$H NMR and as 70:30 mixture of cyclopropane isomers 300 MHz $^1$H NMR (tms=0 ppm) 1.15 (s, 3H) 1.2 (m, 1H); 1.4 (m, 1H); 1.65 (m, 1H); 2.0(s, 3H); 2.9 (d, 3H); 4.0 (s, 3H); 5.0 (s, 2H); 6.8 (bs, 1H); 7.1–7.3 (m, 5H); 7.35–7.6 (m, 3H).

EXAMPLE 7

Preparation of Methyl 2-[2-((trans-1-(2-phenyl-2-methylcyclopropyl)ethylidene)aminooxymethyl)phenyl]-2-methoxyiminoacetate Compound 2.11 of Table 2

To a 25 ml reaction vial equipped with magnetic stirrer were charged 217mg (1.25 mmole) of the trans-1-phenyl-1-methyl-2-acetylcyclopropane and 298 mg (1.25 mmole) of the methyl (E)-2-(aminooxymethyl)phenyl glyoxylate O-methyloxime in 5 ml of anhydrous methanol and 1 drop glacial acetic acid. The reaction was monitored by GC and after 3 hours 90 mg more of the methyl 2-(bromomethyl)phenyl glyoxylate O-methyloxime was added and 5 drops of glacial acetic acid. After stirring 20 hours no more starting material ketone remained and the reaction was worked up. The methanol was removed in vacuuo on the rotary evaporator. To the residue was added 100 ml ethyl acetate and 50 ml water, partitioned, further washed the organic phase with 3×50 ml water, dried over anhydrous MgSO$_4$, filtered and concentrated in vacuuo on the rotary evaporator to give 0.6 g of yellow oil with solid which was chromatographed on silica with 30:70 ethyl acetate:hexane. The pure fractions were combined to afford 260 mg of a clear oil (isolated yield 52.8%) whose NMR was consistent with methyl 2-[2-((trans-1-(2-phenyl-2-methyl-cyclopropyl)ethylidene)aminooxymethyl)phenyl]-2-methoxyiminoacetate as a mixture of isomers, A>B.

NMR (300 MHz $^1$H CDCl3): 1.1–1.4 (m, 5H); 1.75 (m, 1H); 2.0 (s, 3H); 3.85 (s, 3H); 4.05 (s, 3H); 5.0 (s, 2H); 7.1–7.5 (m, 9H).

EXAMPLE 8

Preparation of (E,E and Z,E)-N-Methyl 2-[2-((trans-1-(2-phenyl-2-methyl-cyclopropyl)ethylidene)aminooxymethyl)phenyl]-2-methoxyiminoacetamide Compound 3.11 of Table 3

To a 25 ml reaction test tube under nitrogen atmosphere were charged 160 mg of the methyl 2-[2-((trans-1-(2-phenyl-2-methyl-cyclopropyl)ethylidene)aminooxymethyl)phenyl]-2-methoxyiminoacetate (0.41 mmole) in 3 ml MeOH and 315 mg 40% aqueous methyl amine (4.1 mmole) which was heated at 55–60 C. Monitored by TLC and worked up after 1.5 hours. Removed the methanol in vacuuo on the rotary evaporator at 30 C. To the residue was added 125 ml ethyl acetate and 50 ml water, partitioned, further washed the organic phase with 2×50 ml water, dried over anhydrous MgSO$_4$, filtered and concentrated in vacuuo on the rotary evaporator at 40 C. to afford 130 mg (isolated yield 80.7%) of (E,E and Z,E)-N-methyl 2-[2-((trans-1-(2-phenyl-2-methyl-cyclopropyl)ethylidene)aminooxymethyl)phenyl]-2-methoxyiminoacetamide as a clear oil in a 4:1 ratio of isomers A to B (E,E:Z,E).

NMR (300 MHz $^1$H CDCl3): 1.1–1.4 (m, 5H); 1.75 (m, 1H); 1.95 (s, 3H); 2.9 (d, 3H); 3.95 (s, 3H); 5.0 (s, 2H); 6.7 (bs, 1H); 7.1–7.5 (m, 9H).

Proton NMR data (300 MHz) are provided in Table 13 for typical examples of Tables 1 to 12 and are illustrative of the present invention*

TABLE 13

| Compd # | NMR DATA |
| --- | --- |
| 2.11 | 1.1–1.4 (m, 5H); 1.75 (m, 1H); 2.0 (s, 3H); 3.85 (s, 3H); 4.05 (s, 3H); 5.0 (s, 2H); 7.1–7.5 (m, 9H). |
| 2.14A | 1.15 (s, 3H) .1.2 (m, 1H); 1.4 (m, 1H); 1.6 (m, 1H); 2.0 (s, 3H); 3.85 (s, 3H); 4.0 (s, 3H); 5.0 (s, 2H); 7.1–7.3 (m, 5H); 7.35–7.6 (m, 3H). |
| 3.11 | 1.1–1.4 (m, 5H); 1.75 (m, 1H); 1.95 (s, 3H); 2.9 (d, 3H); 3.95 (s, 3H); 5.0 (s, 2H); 6.7 (bs, 1H); 7.1–7.5 (m, 9H). |
| 3.14A | 1.15 (s, 3H) 1.2 (m, 1H); 1.4 (m, 1H); 1.65 (m, 1H); 2.0 (s, 3H); 2.9 (d, 3H); 4.0 (s, 3H); 5.0 (s, 2H); 6.8 (bs, 1H); 7.1–7.3 (m, 5H); 7.35–7.6 (m, 3H). |

TABLE 13-continued

| Compd # | NMR DATA |
|---|---|
| 8.1 | 1.3 (m, 1H); 1.7 (m, 1H); 1.85 (s, 3H); 1.95 (m, 1H); 2.2 (m, 1H); 3.85 (s, 3H), 4.1 (s, 3H); 5.0 (s, 2H); 7.1 (m, 1H), 7.2 (m, 1H); 7.3 (d, 2H); 7.4–7.6 (m, 3H). |
| 8.1A | 1.19–1.30 (1H, m), 1.50–1.58 (1H, m), 1.75–1.85 (1H, m) 1.84 (3H, s), 2.06–2.14 (1H, m), 3.85 (3H, s), 4.05 (3H, s), 4.98 (2H, s), 7.03–7.49 (7H, m). |
| 8.1B | 1.21–1.28 (1H, m), 1.40–1.52 (1H, m), 1.70 (3H, s), 2.18–2.23 (1H, m) 2.61–2.70 (1H, m), 3.80 (3H, s), 4.00 (3H, s), 4.97 (2H, s), 7.05–7.52 (7H, m). |
| 8.7 | 1.4 (t, 2H); 1.65–1.8 (d, 3H); 2.1 (m, 2H); 3.8 (d, 3H); 4.0 (d, 3H); 5.0 (s, 2H); 6.8 (m, 2H), 7–7.2 (m, 2H); 7.3–7.5 (m, 3H). |
| 9.1 | 1.2 (m, 1H); 1.6 (m, 1H); 1.8 (s, 3H); 1.9 (m, 1H); 2.2 (m, 1H); 2.9 (d, 3H); 3.95 (s, 3H), 5.0 (s, 2H); 6.7 (bs, 1H); 7.1 (m, 1H), 7.2 (m, 1H); 7.3 (d, 2H); 7.4–7.6 (m, 3H). |
| 9.1A | 1.20–1.30 (1H, m), 1.51–1.58 (1H, m), 1.80–1.89 (1H, m), 1.82 (3H, s), 2.2 (1H, m), 2.89 (3H, d), 3.96 (3H, s), 4.98 (2H, s), 6.70 (1H, br), 7.05–7.48 (7H, m). |
| 9.1B | 1.22–1.30 (1H, m), 1.40–1.51 (1H, m), 1.70 (3H, s), 2.15–2.23 (1H, m), 2.60–2.69 (1H,m), 2.85 (3H, d), 3.90 (3H, s), 4.97 (2H, s), 6.70 (1H, br), 7.09–7.51 (7H, m). |
| 9.7A | 1.4 (t, 2H); 1.8 (s, 3H); 2.1 (m, 2H); 2.9 (d, 3H); 3.9 (s, 3H); 4.9 (s, 2H); 6.7 (bs, 1H); 6.8 (t, 2H); 7–7.2 (m, 2H); 7.3–7.5 (m, 3H). |
| 9.7B | 1.3 (m, 1H); 1.6 (m, 4H); 2.1 (m, 1H); 2.8 (m, 4H); 3.9 (s, 3H); 4.9 (s, 2H); 6.7 (bs, 1H); 6.8 (t, 2H); 7–7.2 (m, 2H); 7.3–7.5 (m, 3H). |

*NMR data for compounds designated by A or B are data for one single stereoisomer for $R_2C\!=\!N\!-\!O$. Compounds without designation are a mixture of stereoisomers and the data provided is for the major isomer.

EXAMPLE 10

Numerous compounds of this invention were tested for fungicidal activity in vivo against the diseases described below. The compounds were dissolved in a 1:1 mixture of acetone and methanol 2:1:1 or N,N-dimethylformamide and diluted with a 2:1:1 mixture of water, acetone and methanol (by volume) to achieve the appropriate concentration. The solution was sprayed onto the plants and allowed to dry for two hours. Then the plants were inoculated with fungal spores. Each test utilized control plants which were sprayed with the appropriate solvent and inoculated. For these protective tests, the plants were inoculated one day after treating the plants with the compounds of this invention. The remainder of the technique of each of the tests is given below along with the results for various compounds described herein by the Compound # against the various fungi at a dose of 150 grams per hectare. The results are percent disease control as compared to the untreated check wherein one hundred was rated as complete disease control and zero as no disease control. The application of the test fungal spores to the test plants was as follows:

Wheat Leaf Rust (WLR)

*Puccinia recondita* (f sp. tritici) was cultured on 7-day old wheat (cultivar Fielder) over a 12-day period in the greenhouse. Spores were collected from the leaves by settling on aluminum foil. The spores were cleaned by sieving through a 250-micron opening screen and stored dry. The dried spores were used within one month. A spore suspension was prepared from dry uredia by adding 20 mg (9.5 million spores) per ml of Soltrol oil. The suspension was dispensed into gelatin capsules (0.7 ml capacity) which attach to the oil atomizers. One capsule is used per flat of twenty 2-inch square pots of 7-day old plants, cultivar Fielder. After waiting for at least 15 minutes for the oil to evaporate from the wheat leaves, the plants were placed in a dark mist chamber (18–20° C. and 100% relative humidity) for 24 hours. The plants were then placed in the greenhouse and evaluated after 12 days for disease.

Wheat Leaf Blotch (SNW)

Cultures of *Septoria nodorum* was maintained on Czapek-Dox V-8 juice agar plates in an incubator at 20° C. with alternating periods of 12 hours of light and 12 hours of darkness for 2 weeks. A water suspension of the spores was obtained by shaking the portion of the plate with fungal material in deionized water and filtering through cheesecloth. The spore-containing water suspension was diluted to a spore concentration of $3.0\times10^6$ spores per ml. The inoculum was dispersed by a DeVilbiss atomizer over one-week old Fielder wheat plants which had been previously sprayed with the fungicide compound. The inoculated plants were placed in a humidity cabinet at 20° C. with alternating 12 hours of light and 12 hours of darkness for 7 days. The inoculated seedlings were then moved to a controlled environment room at 20° C. for 2 days of incubation. Disease control values were recorded as percent control.

Wheat Powdery Mildew (WPM)

*Erysiphe graminis* (f. sp. tritici) was cultured on wheat seedlings, cultivar Fielder, in a controlled temperature room at 18° C. Mildew spores were shaken from the culture plants onto 7-day old wheat seedlings which had been previously sprayed with the fungicide compound. The inoculated seedlings were kept in a controlled temperature room at 18° C. and subirrigated. The percent disease control. was rated 7 days after the inoculation. Disease control values were recorded as percent control.

Cucumber Powdery Mildew (CPM)

*Sphaerotheca fulginea* was maintained on cucumber plants, cultivar Bush Champion, in the greenhouse. Inoculum was prepared by placing five to ten heavily mildewed leaves in a glass jar with 500 ml of water containing 1 drop of Tween 80 (polyoxyethylene monooleate) per 100 ml. After shaking the liquid and leaves, the inoculum was filtered through cheese cloth and misted onto the plants with a squirt bottle mister. The spore count was 100,000 spores/ml. The plants were then placed in the greenhouse for infection and incubation. The plants were scored seven days after inoculation. Disease control values were recorded as percent control.

Tomato Late Blight (TLB)

Cultures of *Phytophthora infestans* were maintained on green pea-amended agar for two to three weeks. The spores were washed from the agar with water and dispersed with a DeVilbiss atomizer over the leaves of 3-week old Pixie tomato plants which had been previously treated with compound of the present invention. The inoculated plants were placed in a humidity cabinet at 20° C. for 24 hours for infection. The plants were then removed to a controlled environment room at 20° C. and 90% humidity. The plants were scored for disease control after five days.

Grape Downy Mildew (GDM)

*Plasmopara viticola* was maintained leaves of grape plants, cultivar Delaware, in a controlled temperature chamber at 20° C. in humid air with moderate light intensity for 7 to 8 days. A water suspension of the spores from infested leaves was obtained and the spore concentration was adjusted to about $3\times10^5$ per ml of water. Delaware grape plants were inoculated by spraying the underside of leaves with a De Vilbiss atomizer until small drops were observed on the leaves. The inoculated plants were incubated in a mist chamber for 24 hours at 20° C. The plants were then removed to a controlled environmental room at 20° C. Disease control values were recorded as percent control seven days after inoculation.

Rice Blast (PB)

Cultures of *Pyricularia oyrzae* were maintained on potato dextrose agar for two to three week. The spores were washed from the agar with water containing 1 drop of Tween 80 per 100 ml. After filtering the spore suspension through two layers of cheese cloth, the spore count was adjusted to $5\times10^5$ per ml of water. The spore suspension was sprayed onto 12-day old rice plants, cultivar M-1, using a DeVilbiss atomizer. The inoculated plants were placed in a humidity at chamber 20° C. for 36 hours to allow for infection. After the infection period the plants were placed in the greenhouse. After 6 days, the plants were scored for disease control. Disease control values were recorded as percent control.

Cucumber Downy Mildew (CDM)

Cucumber plants were maintained in the greenhouse. Large, fully expanded leaves were collected from the plates. The stems were wrapped with cotton, the leaves were placed in a large petri plate (15 cm. diameter) and the leaves were supported by glass rods. The upper cover of the plate was removed and the upper surface of the detached cucumber leaf was sprayed with the compounds of the present invention. The leaf was allowed to dry in the air for approximately 2 hours. The cultures of *Pseudoperonospora cubensis* were maintained on cucumber plants. After extracting the spores by shaking the leaves in water, the lower surface of the treated cucumber leaves were sprayed with a spore concentration of 100,000 spores per ml of water. The plates were returned to a controlled environmental chamber at 20° C. and 90% humidity for five days. After this time, leaves were examined for disease development. Disease control values were recorded as percent control.

Cucumber Anthracnose (CA)

The fungal pathogen *Colletotrichum lagenarium* was cultured on potato dextrose agar (PDA) in the dark at 22 C. for a period of 8 to 14 days. Spores of *C. lagenarium* were removed from the PDA plates by flooding the plate surface with distilled water, amended with 0.5% v/w of yeast extract. The upper surface of the fungal colony was scraped with a blunt instrument until most of the spores were released into the aqueous environment. The spore suspension was filtered though cheesecloth, and the spore count was adjusted by adding more water, containing the yeast extract, until $3.0\times10^6$ spores per ml of water was achieved.

The chemically-treated cucumber plants were 15-days old, cultivar Bush Champion. The upper leaf surface of the plants were sprayed with the spore suspension until runoff, using a hand-held pump spray bottle. The plants were placed in a fluorescent-lighted mist chamber (12 hr light, 12 hr dark) for 48 hours. After that infection period, the plants were placed in a growth chamber for 3 days at 25 C. and 90% humidity. The treated plants were then evaluated for disease control. Disease control values were recorded as percent control.

When tested against wheat leaf rust at 150 grams per hectare compounds 3.11, 3.14A, 9.1, and 9.7A exhibited 100% control.

When tested against wheat leaf blotch at 150 grams per hectare compounds 3.11, 3.14A, 9.1, 9.7A, and 9.8 exhibited 90% or better control.

When tested against wheat powdery mildew at 150 grams per hectare compounds 9.1, and 9.7A exhibited 90% or better control.

When tested against cucumber powdery mildew at a dose of 150 grams per hectare compounds 3.11, 3.14A, 8.1, 9.1, and 9.7A exhibited 100% control.

When tested against tomato late blight at 150 grams per hectare compounds 3.11, 3.14A, 8.1, 9.1, 9.7A, and 9.8 exhibited 95% or better control.

When tested against grape downy mildew at 150 grams per hectare compounds 9.1, and 9.7A exhibited 100% or better control.

When tested against rice blast at 150 grams per hectare compounds 3.11, 3.14A, 8.1, 9.1, and 9.7A exhibited 95% or better control.

When tested against cucumber downy mildew at 150 grams per hectare compounds 3.11, 3.14A, 9.1, and 9.8 and exhibited 95% or better control and when tested at 9 grams per hectare compound 9.7A exhibited 100% control.

When tested against cucumber anthracnose at 150 grams per hectare compounds 3.11, 3.14A, 9.1, 9.7A and 9.8 exhibited 100% control.

The compounds of this invention are useful as agricultural fungicides and, as such, can be applied to various loci such as the seed, the soil or the foliage of plants to be protected.

The compounds of this invention can be applied as fungicidal sprays by methods commonly employed, such as conventional high-volume hydraulic sprays, low-volume sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20, preferably from about 0.05 to about 4, and more preferably from about 0.1 to about 1 grams per hundred kilograms of seed. As a soil fungicide the chemical can be incorporated in the soil or applied to the surface usually at a rate of from about 0.02 to about 20, preferably from about 0.05 to about 10, and more preferably from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare.

Inasmuch as the compounds of this invention display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15). Other known fungicides which an be combined with the compounds of this invention are dimethomorph, cymoxanil, thifluzamide, furalaxyl, ofurace, benalaxyl, oxadixyl, propamocarb, cyprofuram, fenpiclonil, fludioxonil, pyrimethanil, cyprodinil, triticonazole, fluquinconazole, metconazole, spiroxamine, carpropamid, azoxystrobin, kresoxim-methyl, metominostrobin and trifloxystrobin.

The compounds of this invention can be advantageously employed in various ways. Since these compounds possess broad spectrum fungicidal activity, they can be employed in the storage of cereal grain. These compounds can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, barley stripe and leaf rust, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast.

Compositions and formulations according to the present invention may also include known pesticidal compounds. This expands the spectrum of activity of the preparation and may give rise to synergism. Suitable insecticides known in the art include those listed in U.S. Pat. No. 5,075,471, see in particular columns 14 and 15.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse of diffuse the active ingredient in the composition without impairing the active ingredient's effectiveness and which by itself has no significant detrimental effect on the soil, equipment, desirable plants, or agronomic environment. If desired, adjuvants such as surfactants, stabilizers, antifoam agents and anti-drift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instant invention.

It is usually desirable, particularly in the case of foliar spray formulations, to include adjuvants, such as wetting agents, spreading agents, dispersing agents, stickers, adhesive and the like in accordance with agricultural practices. A listing of such adjuvants commonly used in the art, and a discussion of adjuvants, can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001 (1:999,999)–99 (99:1) % by weight. For compositions suitable for storage or transportation, the amount of active ingredient is preferably between about 0.5 (1:199)–90 (9:1) % by weight, and more preferably between about 1 (1:99)–75 (3:1) % by weight of the mixture. Compositions suitable for direct application or field application generally contain the active compound in an amount substantially between about 0.0001 (1:999,999)–95 (19:1) %, preferably between about 0.0005 (1:199,999)–90 (9:1) % by weight, and more preferably between about 0.001 (1:99,999)–75 (3:1) % by weight of the mixture. The composition can also be stated as a ratio of the compound to the carrier. In the present invention the weight ratio of these materials (active compound/carrier) can vary from 99:1 (99%) to 1:4 (20%) and more preferably from 10:1 (91%) to 1:3 (25%).

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clay, inorganic silicate and carbonate, and silica and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a compound of Formula I, 45 parts of a synthetic precipitated hydrated silicon dioxide and 5 parts of sodium lignosulfonate. In another preparation a kaolin type (Barden) clay is used in place of the synthetic precipitated hydrated silicon dioxide in the above wettable powder, and in another such preparation 25% of the silicon dioxide is replaced with a synthetic sodium silicoaluminate.

Dusts are prepared by mixing compounds of Formula I, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

We claim:
1. A compound of the formula:

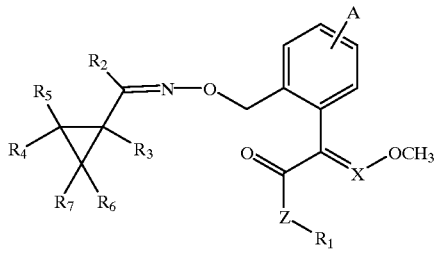

wherein X is N or CH; Z is O, S, or $NR_8$;
A is hydrogen, halo, cyano, $(C_1-C_{12})$alkyl, or $(C_1-C_{12})$alkoxy;
$R_1$ and $R_8$ are independently hydrogen or $(C_1-C_4)$alkyl;
$R_2$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, or cyano;
$R_3$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, or halo$(C_2-C_8)$alkynyl;
$R_4$ and $R_5$ are independently hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, halo, cyano, or $(C_1-C_4)$alkoxycarbonyl; and wherein
A) $R_7$ is aryl, arylalkyl, heterocyclic or heterocyclic $(C_1-C_4)$alkyl wherein the aryl or heterocyclic ring is substituted with from 2 to 5 substituents and wherein the positions on the aryl and heterocyclic rings adjacent to the bond to the cyclopropyl ring are both substituted and $R_6$ is hydrogen, $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, or halo$(C_2-C_8)$alkynyl; or
B) $R_7$ is aryl, arylalkyl, heterocyclic or heterocyclic $(C_1-C_4)$alkyl wherein the aryl or heterocyclic ring is unsubstituted or substituted from 1 to 4 substituents wherein at least one of the positions adjacent to the bond to the cyclopropyl ring is a hydrogen and $R_6$ is selected from the group consisting of $(C_1-C_{12})$alkyl, halo$(C_1-C_{12})$alkyl, $(C_3-C_7)$cycloalkyl, halo$(C_3-C_7)$cycloalkyl, $(C_2-C_8)$alkenyl, halo$(C_2-C_8)$alkenyl, $(C_2-C_8)$alkynyl, or halo$(C_2-C_8)$alkynyl;
and their salts, complexes, enantiomorphs, and stereoisomers; and mixtures thereof.

2. The compound of claim 1 wherein X is CH, Z is O, $R_2$ is $(C_1-C_{12})$alkyl, and $R_3$ is H.

3. The compound of claim 2 wherein $R_7$ is 2,6-dichlorophenyl, 2,6-difluorophenyl, 2,6-dibromophenyl, 2,6-bis(trifluoromethyl)phenyl, 2,3,6-trichlorophenyl, 2,3,6-trifluorophenyl, 2,3,6-tribromophenyl, 2,3,6-tris(trifluoromethyl)phenyl, 2,4,6-trichlorophenyl, 2,4,6-trifluorophenyl, 2,4,6-tribromophenyl, or 2,4,6-tris(trifluoromethyl)phenyl.

4. The compound of claim 1 wherein X is N, Z is O or NH, $R_2$ is $(C_1-C_{12})$alkyl and $R_3$ is H.

5. The compound of claim 4 wherein $R_7$ is 2,6-dichlorophenyl, 2,6-difluorophenyl, 2,6-dibromophenyl, 2,6-bis(trifluoromethyl)phenyl, 2,3,6-trichlorophenyl, 2,3,6-trifluorophenyl, 2,3,6-tribromophenyl, 2,3,6-tris(trifluoromethyl)phenyl, 2,4,6-trichlorophenyl, 2,4,6-trifluorophenyl, 2,4,6-tribromophenyl, or 2,4,6-tris(trifluoromethyl)phenyl.

6. The compound of claim 1 where the compound is N-methyl-2-[2-((trans-1-(2-(2',6'-dichloromethylphenyl)cyclopropyl)ethylidene)aminooxymethyl)phenyl]-2-methoxyiminoacetamide.

7. The compound of claim 2 wherein $R_6$ is $(C_1-C_{12})$alkyl and $R_7$ is phenyl, 2-chlorophenyl, 3-chlorophenyl, 4-chlorophenyl, 4-fluorophenyl, 4-bromophenyl, 2-(trifluoromethyl)phenyl, 2,4-dichlorophenyl, 2,4-difluorophenyl, 2,4-dibromophenyl, or 2,4-bis(trifluoromethyl)phenyl.

8. The compound of claim 4 wherein $R_6$ is $(C_1-C_{12})$alkyl and $R_7$ is phenyl, 2-chlorophenyl, 3-chlorophenyl, 4-chlorophenyl, 4-fluorophenyl, 4-bromophenyl, 2-(trifluoromethyl)phenyl, 2,4-dichlorophenyl, 2,4-difluorophenyl, 2,4-dibromophenyl, or 2,4-bis(trifluoromethyl)phenyl.

9. The compound of claim 1 where the compound is N-methyl 2-[2-((trans-1-(2-phenyl-2-methylcyclopropyl)ethylidene)aminooxymethyl)phenyl]-2-methoxyiminoacetamide.

10. A method of preparation of the compounds of claim 4 wherein X is N, Z is O, and $R_6$ is $(C_1-C_{12})$alkyl comprising the step of reacting methyl (E)-2-(aminooxymethyl)phenyl glyoxylate O-methyloxime with a 1-aryl or 1-heteroaryl-1-$(C_1-C_{12})$alkyl-2-((C=O)$(C_1-C_{12})$alkyl)cyclopropane.

11. A fungicidal composition for controlling phytopathogenic fungi which comprises an agronomically acceptable carrier and the compound of claim 1 wherein the ratio of the carrier to the compound is between 99:1 and 1:4.

12. A method for controlling phytopathogenic fungi which comprises applying the compound of claim 1 to the locus where control is desired, at a rate of from 0.005 to 50 kilograms per hectare.

* * * * *